United States Patent
Xu

(10) Patent No.: US 9,790,270 B2
(45) Date of Patent: Oct. 17, 2017

(54) SODIUM PUMP ANTIBODY AGONISTS AND METHODS OF TREATING HEART DISEASE USING THE SAME

(71) Applicant: Kai Yuan Xu, Cockeysville, MD (US)

(72) Inventor: Kai Yuan Xu, Cockeysville, MD (US)

( * ) Notice: Subject to any disclaimer, the term of this patent is extended or adjusted under 35 U.S.C. 154(b) by 0 days.

(21) Appl. No.: 14/960,664

(22) Filed: Dec. 7, 2015

(65) Prior Publication Data

US 2016/0083463 A1    Mar. 24, 2016

Related U.S. Application Data

(62) Division of application No. 14/692,584, filed on Apr. 21, 2015, now Pat. No. 9,238,695, which is a division of application No. 13/359,723, filed on Jan. 27, 2012, now Pat. No. 9,040,046.

(60) Provisional application No. 61/437,719, filed on Jan. 31, 2011.

(51) Int. Cl.
C07K 16/18 (2006.01)
C07K 16/40 (2006.01)
A61K 39/00 (2006.01)

(52) U.S. Cl.
CPC .............. *C07K 16/18* (2013.01); *C07K 16/40* (2013.01); *A61K 2039/505* (2013.01); *C07K 2317/21* (2013.01); *C07K 2317/24* (2013.01); *C07K 2317/34* (2013.01); *C07K 2317/75* (2013.01)

(58) Field of Classification Search
CPC .... C07K 16/18; C07K 16/40; C07K 2317/34; C07K 2317/75; C07K 2317/21; A61K 2039/505
See application file for complete search history.

(56) References Cited

U.S. PATENT DOCUMENTS

| | | | | |
|---|---|---|---|---|
| 7,754,210 B2 * | 7/2010 | Xu | .......................... | C07K 16/40 424/133.1 |
| 9,040,046 B2 * | 5/2015 | Xu | .......................... | C07K 16/40 424/133.1 |
| 9,238,695 B2 * | 1/2016 | Xu | .......................... | C07K 16/40 |

OTHER PUBLICATIONS

Young et al., Multiple mRNAs from rat kidney and brain encode a single Na+, K+—ATPase beta subunit protein. J. Biol. Chem. 262:4905-4910, 1987.*
Xu, Biochem. Activation of (Na+ + K+)—ATPase. Biophys. Res. Commun. 338:1669-1677, 2005.*
Xu, Biochem. Biophys. Res. Commun. 415:479-484, 2011.*

* cited by examiner

*Primary Examiner* — Ruixiang Li

(57) ABSTRACT

Antibodies that are agonists of sodium pump ($Na^+/K^+$ ATPase; NKA) activity are provided. In particular, antibodies that specifically bind epitopes on the beta-1 ($\beta_1$) subunit of NKA are disclosed. These antibodies have the ability to increase the activity of the catalytic alpha subunit of NKA upon $\beta_1$ subunit binding. Due to their activity, the antibodies also have the ability to trigger a positive inotropic effect in cardiac tissues (i.e., increase cardiac contraction). The present invention thus includes, but is not limited to, NKA $\beta_1$ subunit peptide epitopes, antibodies that specifically bind the epitopes, methods of agonizing NKA activity through administration of the peptides or the antibodies, and methods of treating and/or preventing heart disease through administration of the peptides or the antibodies.

6 Claims, 10 Drawing Sheets

Figure 1
A
| Rat | β₁ | ¹³⁴KERGEFNHERGER¹⁴⁶ |
| Human | β₁ | ¹³⁴KERGDFNHERGER¹⁴⁶ |
| Dog | β₁ | ¹³⁴KERGEFNNERGER¹⁴⁶ |
| Pig | β₁ | ¹³⁴KERGEYNNERGER¹⁴⁶ |
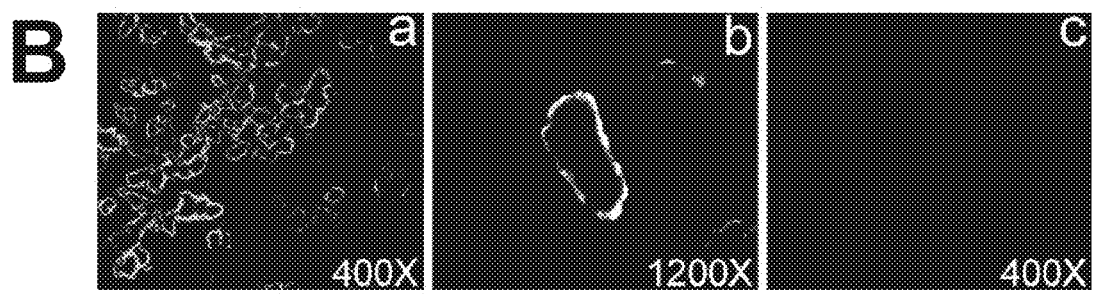
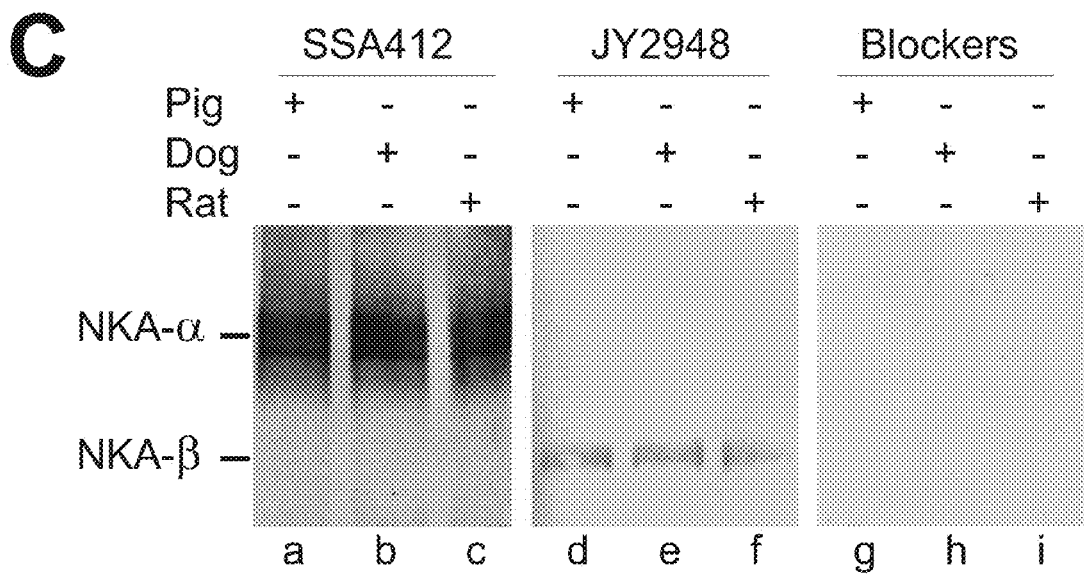

Figure 2A-B
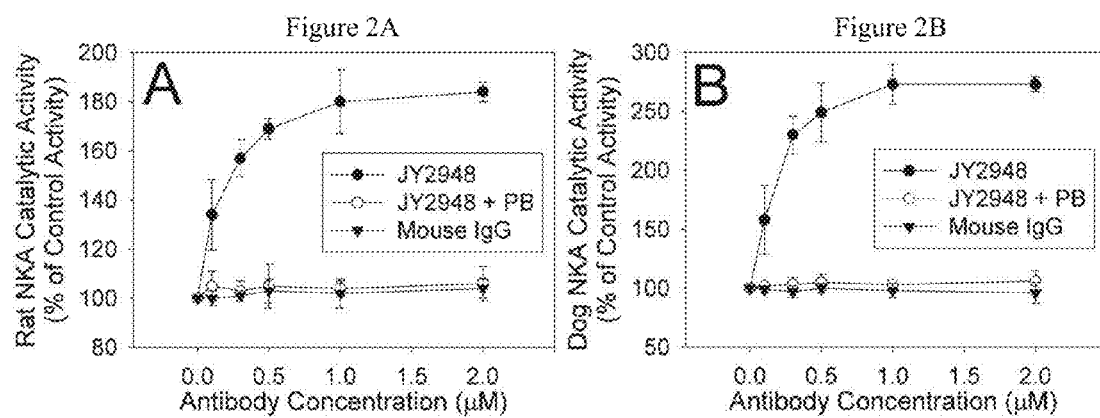
Figure 2C-D
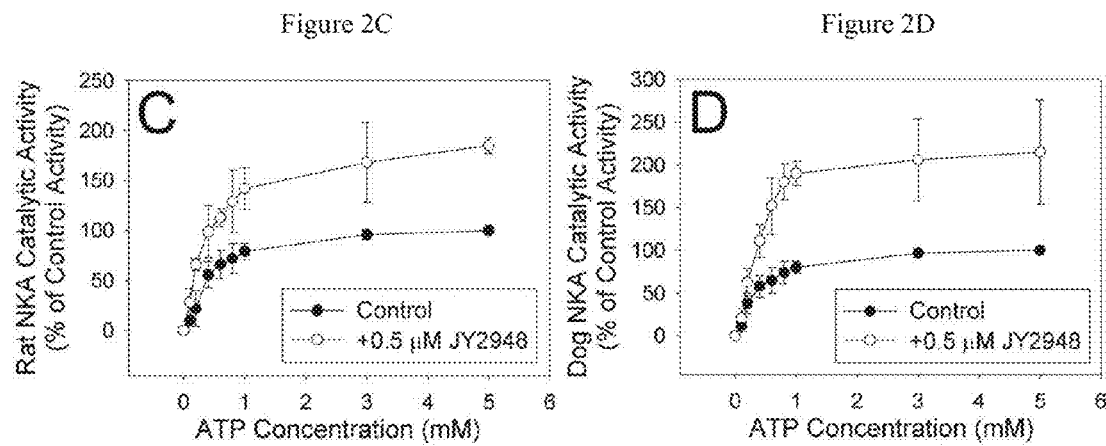

SODIUM PUMP ANTIBODY AGONISTS AND METHODS OF TREATING HEART DISEASE USING THE SAME

TECHNICAL FIELD

The invention relates to antibodies that are agonists of sodium pump ($Na^+/K^+$ ATPase; NKA) activity, methods of agonizing NKA activity using the antibodies, and methods of treating heart disease using the antibodies.

BACKGROUND OF INVENTION

The ($Na^+$+$K^+$-ATPase (NKA; the Na pump) is a transmembrane enzyme responsible for the active reciprocal transport of $Na^+$ and $K^+$ ions across the plasma membrane of all animal cells (1, 2). This key enzyme is composed of two different subunits. The α subunit (~113 kDa) contains the binding sites for ATP, $Na^+$ ions, $K^+$ ions, and allosteric sites for inhibitors and activators, and is capable of catalyzing the hydrolysis of ATP as an essential energy source to transport 3 $Na^+$ ions out of the cell and 2 $K^+$ ions into the cell against membrane ion gradients (1, 2, 6, 7). All tissue-specific isoforms of the NKA α subunit (α1, α2, α3, α4) share the same catalytic function and active ion transporting properties to maintain cell membrane potential, control cell volume, and provide a driving force for the secondary membrane transporters to import glucose, amino acids, and other nutrients into the cell (8-11). The smaller beta (β) subunit (~35 kDa) is a glycoprotein (12-15). Isoforms of NKA β subunit (β1, β2, β3) do not have binding sites for ATP or $Na^+/K^+$ ions, and therefore do not operate the catalytic process and $Na^+/K^+$ active transport of the enzyme (6).

Because ionic transport via sodium pumps creates both an electrical and chemical gradient across the plasma membrane, the NKA is especially important for the proper function of the cardiac muscle. Abnormalities in the number or function of NKA are thought to be involved in a number of pathologic conditions, such as heart disease and hypertension. For example, several types of heart failure are associated with significant reductions in myocardial concentrations of NKA and low levels of NKA activity.

Additional diseases associated with significantly reduced NKA activity include diabetes, lung diseases, liver diseases, urinary tract diseases, hemorrhagic shock, gastrointestinal diseases including colitis, cataracts, Alzheimer's disease, eye disease, aging, cancer, kidney diseases, obesity and diseases of the nervous system.

Due to its association with heart disease, NKA has been a target for the treatment of congestive heart failure, such as through the administration of digitalis and related cardiac glycoside drugs (3-5). Cardiac glycosides have the ability to increase the force of myocardial contraction in a dose-dependent manner (positive inotropic effect) via direct inhibition of NKA (16). Such action inhibits the excretion of cellular sodium, thereby increasing intracellular sodium and calcium through increased activity of the sodium calcium exchanger. The increased intracellular calcium, in turn, increases cardiac contraction. Thus, circulation is increased in patients suffering from a weakened heart muscle, such as those with congestive heart failure, receiving these drugs.

However, cardiac glycosides have narrow therapeutic indices and their use is frequently accompanied by toxic effects that can be severe or lethal. The most important toxic effects, in terms of risk to the patient, are those that involve the heart (e.g., abnormalities of cardiac rhythm and disturbances of atrio-ventricular conduction). Gastrointestinal disorders, neurological effects, anorexia, blurred vision, reduced renal function, nausea and vomiting are other common cardiac glycoside-induced reactions.

Other drugs used to treat heart failure also have dangerous side effects. For example, diuretics are associated with fatigue, low blood pressure, and poor kidney function. ACE inhibitors are associated with persistent cough, kidney problem, fatigue, and dizziness. Beta blockers are associated with fatigue, low blood pressure, dizziness, chest pain, and headaches.

Consequently, there is a need for new agents which overcome the drawbacks associated with known agents.

BRIEF SUMMARY OF INVENTION

The present invention provides antibodies that are agonists of sodium pump ($Na^+/K^+$ ATPase; NKA) activity. In particular, antibodies that specifically bind epitopes on the $β_1$ subunit of NKA are disclosed. These antibodies have the ability to increase the activity of the catalytic alpha subunit of NKA upon $β_1$ subunit binding. Due to their activity, the antibodies also have the ability to trigger a positive inotropic effect in cardiac tissues (i.e., induce and/or strengthen cardiac contraction). The present invention thus includes, but is not limited to, NKA $β_1$ subunit peptide epitopes, antibodies that specifically bind the epitopes, methods of agonizing NKA activity through administration of the peptides or the antibodies, and methods of treating heart disease and other diseases through administration of the peptides or the antibodies.

In particular, the invention provides isolated and/or purified antibodies that specifically bind the $β_1$ subunit of NKA and that have NKA agonizing activity. In certain aspects of the invention, upon binding to the $β_1$ subunit of NKA the antibodies of the invention also have the ability to: (i) increase cardiac myocyte intracellular $Ca^{2+}$ concentration, (ii) induce positive inotropic effect, and (iii) increase the force of cardiac contraction. The antibodies include polyclonal antibodies, monoclonal antibodies, human antibodies, humanized and chimeric versions thereof and fragments thereof.

The invention provides isolated and/or purified antibodies that specifically bind an epitope of the $β_1$ subunit of NKA comprising the amino acid sequence KERGEFNHERGER (SEQ ID NO:1; Rat JY2948 epitope) and/or KERGDFNHERGER (SEQ ID NO:2; Human JY2948 epitope). The antibodies have NKA agonizing activity.

The invention provides isolated and/or purified antibodies that specifically bind an epitope of the $β_1$ subunit of NKA comprising the amino acid sequence RDEDKDKVGNIEY (SEQ ID NO:3; Rat JY421228 epitope) and/or RDEDKDKVGNVEY (SEQ ID NO:4; Human JY421228 epitope). The antibodies have NKA agonizing activity.

The antibodies of the invention include polyclonal antibodies, monoclonal antibodies, human antibodies, humanized and chimeric versions thereof and fragments thereof.

In one aspect of the invention, the antibody JY421228 is provided. In another aspect of the invention, the antibody JY2948 is provided. Both antibodies specifically bind the $β_1$ subunit of NKA and both antibodies have NKA agonizing activity. The invention includes human, humanized and chimeric versions of these antibodies and fragments thereof.

The invention provides pharmaceutical formulations comprising one or more of the antibodies of the invention and a pharmaceutically acceptable carrier.

In some aspects, pharmaceutical formulations comprising one or more of the antibodies of the invention are administered to a subject suffering from or susceptible to heart disease and/or a myocyte contractile disorder. Such pharmaceutical formulations can therefore be used in the treatment of a subject suffering from or susceptible to heart disease and/or a myocyte contractile disorder. The pharmaceutical formulations can also be used in the prevention of heart disease and/or a myocyte contractile disorder in a subject.

The invention provides isolated and/or purified peptides consisting of the following amino acid sequences: KERGEFNHERGER (SEQ ID NO:1; Rat JY2948 epitope), KERGDFNHERGER (SEQ ID NO:2; Human JY2948 epitope), RDEDKDKVGNIEY (SEQ ID NO:3; Rat JY421228 epitope) and RDEDKDKVGNVEY (SEQ ID NO:4; Human JY421228 epitope). The invention also provides isolated and/or purified derivatives and/or variants of each of these peptides, wherein the derivatives and/or variants having 5 or fewer amino acid changes, and wherein the changes are individually selected from insertions, deletions and substitutions.

The invention provides immunogenic formulations comprising (i) one or more of the peptides of SEQ ID NOs:1-4 and (ii) a pharmaceutically acceptable carrier and/or adjuvant. The invention also provides immunogenic formulations comprising (i) one or more derivatives and/or variants of the peptides of SEQ ID NOs:1-4, wherein each individual variant has 5 or fewer amino acid changes, and wherein the changes are individually selected from insertions, deletions and substitutions, and (ii) a pharmaceutically acceptable carrier and/or adjuvant. The invention further provides immunogenic formulations comprising (i) one or more of the peptides of SEQ ID NOs:1-4, (ii) one or more of the peptide variants, and (iii) a pharmaceutically acceptable carrier and/or adjuvant.

In some aspects, the immunogenic formulations are used to induce production of NKA $\beta_1$ subunit-binding antibodies in a subject. The immunogenic formulations can be administered to a host as a means for producing NKA $\beta_1$ subunit-binding antibodies that can then be recovered and purified. The immunogenic formulations can also be administered to a subject suffering from or susceptible to heart disease and/or a myocyte contractile disorder as part of a course of treatment. The immunogenic formulations can therefore be used in the treatment of a subject suffering from or susceptible to heart disease and/or a myocyte contractile disorder.

The invention provides expression vectors encoding peptides comprising (or consisting of) one or more of the peptides of SEQ ID NOs:1-4, one or more of the peptide variants thereof as defined herein, or a combination of both. The invention provides pharmaceutical formulations comprising one or more of the vectors and a pharmaceutically acceptable carrier.

In some aspects, the vectors and pharmaceutical formulations comprising the vectors are used to induce production of NKA $\beta_1$ subunit-binding antibodies in a subject. In some aspects, the vectors are under the control of tissue specific promoters, such as cardiac tissue specific promoters. The vectors and pharmaceutical formulations can be administered to a subject suffering from or susceptible to heart disease and/or a myocyte contractile disorder, whereupon the peptides or peptide variants of the invention are produced, followed by production of NKA $\beta_1$ subunit-binding antibodies. The vectors and pharmaceutical formulations can therefore be used in the treatment of a subject suffering from or susceptible to heart disease and/or a myocyte contractile disorder.

The invention provides methods for increasing NKA activity comprising contacting the $\beta_1$ subunit of NKA with an antibody that specifically binds an epitope of the $\beta_1$ subunit and that has NKA agonist activity. The antibodies that may be used in this method include any of the antibodies described herein, such as an antibody that specifically binds one or more of the peptides represented by SEQ ID NOs:1-4, antibody JY421228, or antibody JY2948.

The invention provides methods for inducing cardiac myocyte contraction comprising contacting a cardiac myocyte with an antibody that specifically binds an epitope of the $\beta_1$ subunit of NKA and that has NKA agonist activity. The antibodies that may be used in this method include any of the antibodies described herein, such as an antibody that specifically binds one or more of the peptides represented by SEQ ID NOs:1-4, antibody JY421228, or antibody JY2948.

The invention provides methods for inducing cardiac contraction comprising contacting a heart with an antibody that specifically binds an epitope of the $\beta_1$ subunit of NKA and that has NKA agonist activity. The antibodies that may be used in this method include any of the antibodies described herein, such as an antibody that specifically binds one or more of the peptides represented by SEQ ID NOs:1-4, antibody JY421228, or antibody JY2948.

The invention provides methods for increasing the force of cardiac contraction comprising contacting a heart with an antibody that specifically binds an epitope of the $\beta_1$ subunit of NKA and that has NKA agonist activity. The antibodies that may be used in this method include any of the antibodies described herein, such as an antibody that specifically binds one or more of the peptides represented by SEQ ID NOs:1-4, antibody JY421228, or antibody JY2948.

The invention provides methods for inducing an immune response in a subject, comprising administering to a subject an immunologically effective amount of an immunogenic formulation comprising (i) one or more peptides of SEQ ID NOs:1-4, and/or variants thereof, and (ii) a pharmaceutically acceptable carrier and/or adjuvant.

The invention provides methods for inducing an immune response in a subject, comprising administering to a subject a pharmaceutical formulation comprising (i) one or more vectors encoding one or more peptides SEQ ID NOs:1-4, and/or one or more variants thereof, and (ii) a pharmaceutically acceptable carrier and/or adjuvant.

The invention provides methods for treating heart disease in a subject, comprising administering to a subject in need of treatment a pharmaceutical formulation comprising (i) one or more antibodies that specifically binds the $\beta_1$ subunit of NKA and having NKA agonist activity and (ii) a pharmaceutically acceptable carrier, thereby treating heart disease in a subject. The antibodies that may be used in this method include any of the antibodies described herein, such as an antibody that specifically binds one or more of the peptides represented by SEQ ID NOs:1-4, antibody JY421228, or antibody JY2948.

The invention provides methods for treating heart disease in a subject, comprising administering to a subject in need of treatment an immunogenic formulation comprising (i) one or more peptides of SEQ ID NOs:1-4, and/or variants thereof, and (ii) a pharmaceutically acceptable carrier and/or adjuvant, wherein the immunogenic formulation induces endogenous production of an antibody that specifically binds the $\beta_1$ subunit of Na$^+$/K$^+$ ATPase (NKA) and that has NKA agonizing activity, thereby treating heart disease in a subject.

The invention provides methods for treating heart disease in a subject, comprising administering to a subject in need of treatment a pharmaceutical formulation comprising (i) one or more vectors encoding one or more peptides SEQ ID NOs:1-4, and/or variants thereof, and (ii) a pharmaceutically acceptable carrier, wherein the one or more peptides and/or variants are produced in the subject, followed by induction of endogenous production of an antibody that specifically binds the $\beta_1$ subunit of Na$^+$/K$^+$ ATPase (NKA) and that has NKA agonizing activity, thereby treating heart disease in a subject.

The invention provides methods for preventing heart failure in a subject, comprising administering to a subject in need of prevention a pharmaceutical formulation comprising (i) one or more antibodies that specifically binds the $\beta_1$ subunit of NKA and having NKA agonist activity and (ii) a pharmaceutically acceptable carrier, thereby preventing heart disease in a subject. The antibodies that may be used in this method include any of the antibodies described herein, such as an antibody that specifically binds one or more of the peptides represented by SEQ ID NOs:1-4, antibody JY421228, or antibody JY2948.

The invention provides methods for preventing heart failure in a subject, comprising administering to a subject in need of prevention an immunogenic formulation comprising (i) one or more peptides of SEQ ID NOs:1-4, and/or derivatives and/or variants thereof, and (ii) a pharmaceutically acceptable carrier and/or adjuvant, wherein the immunogenic formulation induces endogenous production of an antibody that specifically binds the $\beta_1$ subunit of Na$^+$/K$^+$ ATPase (NKA) and that has NKA agonizing activity, thereby preventing heart disease in a subject.

The invention provides methods for preventing heart failure in a subject, comprising administering to a subject in need of prevention a pharmaceutical formulation comprising (i) one or more vectors encoding one or more peptides SEQ ID NOs:1-4, and/or variants thereof, and (ii) a pharmaceutically acceptable carrier and/or adjuvant, wherein the one or more peptides and/or variants are produced in the subject, followed by induction of endogenous production of an antibody that specifically binds the $\beta_1$ subunit of Na$^+$/K$^+$ ATPase (NKA) and that has NKA agonizing activity, thereby preventing heart disease in a subject.

The foregoing has outlined rather broadly the features and technical advantages of the present invention in order that the detailed description of the invention that follows may be better understood. Additional features and advantages of the invention will be described herein, which form the subject matter of the claims of the invention.

BRIEF DESCRIPTION OF DRAWINGS

FIG. 1. Specificity of monoclonal antibody JY2948. (A) Antigenic side: JY2948 was made against KERGEFN-HERGER peptide (SEQ ID NO:1), which resides in the extracellular domain of the β1-subunit of NKA and is highly conserved in rat (SEQ ID NO:1), human (SEQ ID NO:2), dog (SEQ ID NO:5) and pig (SEQ ID NO:6). (B) Confocal images of immunofluorescent staining of JY2948 on cross-section of isolated rat cardiac myocytes: a) a group of myocytes at a magnification of 400×, b) a single myocyte at 3000×, c) a group of myocytes stained in the presence of both JY2948 and its peptide blocker. These data represent one of 5 similar immunofluorescent stainings (C) Specificity analysis by Western blotting: a) Pig NKA α1, b) dog NKA α1, and c) rat NKA α1 were detected by a α1-subunit specific antibody SSA412; d) pig NKA β1, e) dog NKA β1, and f) rat NKA β1 were recognized by JY2948; g) pig NKA, h) dog NKA, and i) rat NKA were incubated with both SSA412 and JY2948 in the presence of peptide blockers PB412 and PB2948. The data represent one of 3 similar Western blots. JY2948 only interacts with the β1-subunit of NKA on the extracellular site of the enzyme.

FIG. 2A-B. NKA activity is a function of the concentration of JY2948. Purified rat NKA (A, 5 μg/ml) and dog (B, 0.8 μg/ml) NKA were incubated with different concentrations of JY2948 or mouse IgG with or without peptide blocker PB2948, as indicated in the figures for 60 min prior to ouabain-sensitive ATPase assay in the presence of 100 mM Na$^+$, 20 mM K$^+$, and 3 mM ATP. Effect of JY2948 on the hydrolysis of ATP. The data represent mean±SEM of five independent experiments. Binding of JY2948 to β1-subunit of NKA increases the catalytic function of the enzyme.

FIG. 2C-D. Allosteric effect of the β1 subunit on the hydrolysis of ATP by NKA α1-subunit. Purified rat NKA (C, 5 μg/ml) and dog (D, 0.75 μg/ml) NKA were incubated with 0.5 μM JY2948 at room temperature for 60 min prior to ouabain-sensitive ATPase assay in the presence of 0, 0.2, 0.4, 0.6, 0.8, 1, 3, and 5 mM ATP. The concentrations of Na$^+$ and K$^+$ in the assay were 100 mM and 20 mM, respectively. Each data point represents the mean±SEM of five independent experiments. Binding of JY2948 to the NKA β1-subunit increases the rate of hydrolysis of ATP without changing the Km of ATP.

DETAILED DESCRIPTION OF THE INVENTION

Figure 3:
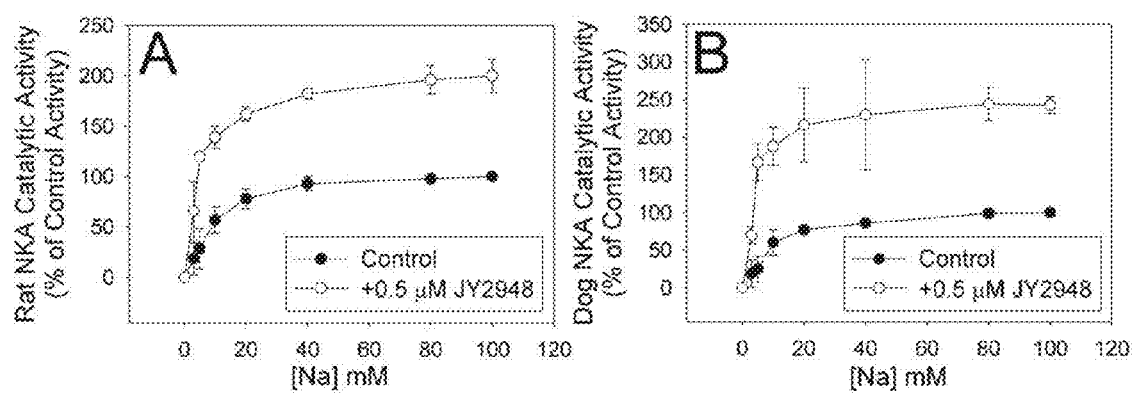
FIG. 3. Allosteric effect of β1 subunit on Na$^+$ affinity of NKA. Purified rat NKA (A, 5 μg/ml) and dog (B, 0.8 μg/ml) NKA were incubated with 0.5 μM JY2948 at room temperature for 60 min prior to ouabain-sensitive ATPase assay in the presence of 0, 3, 5, 10, 20, 40, 80, and 100 mM Na$^+$. The concentrations of K$^+$ and ATP in the assay were 20 mM and 3 mM, respectively. Each data point represents the mean±SEM of five independent experiments. Binding of JY2948 to β1-subunit of NKA increases the NKA Na$^+$ affinity.

Unless otherwise noted, technical terms are used according to conventional usage. Definitions of common terms in molecular biology may be found, for example, in Benjamin Lewin, Genes VII, published by Oxford University Press, 2000 (ISBN 019879276X); Kendrew et al. (eds.); The Encyclopedia of Molecular Biology, published by Blackwell Publishers, 1994 (ISBN 0632021829); and Robert A. Meyers (ed.), Molecular Biology and Biotechnology: a Comprehensive Desk Reference, published by Wiley, John & Sons, Inc., 1995 (ISBN 0471186341); and other similar technical references.

As used herein, "a" or "an" may mean one or more. As used herein when used in conjunction with the word "comprising," the words "a" or "an" may mean one or more than one. As used herein "another" may mean at least a second or more. Furthermore, unless otherwise required by context, singular terms include pluralities and plural terms include the singular.

As used herein, "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

As outlined in a general manner above, the present invention is based on the surprising discovery that antibodies that specifically bind the β₁ subunit of the sodium pump ($Na^+/K^+$ ATPase; NKA) have NKA inducing activity. Thus, the β₁ subunit binding-antibodies are agonists of NKA. These antibodies have the ability to increase the activity of the catalytic alpha subunit of NKA upon β₁ subunit binding. Because these antibodies can increase the activity of the sodium pump, they can be used in the treatment of diseases associated with reduced function of the pump. In a specific example, and due to their NKA inducing activity, the antibodies of the invention can be used to induce and/or increase cardiac contraction and can therefore be used in the treatment of heart disease.

Antibodies

Thus, the invention provides antibodies that specifically bind the β₁ subunit of NKA and that also function as agonists of NKA. The skilled artisan will understand that the particular attributes of the antibodies of the present invention are only confined by (i) the ability to bind with specificity to the β₁ subunit of NKA, and (ii) the ability to function as an agonist of NKA. For example, the antibodies may be polyclonal, monoclonal, humanized or chimeric antibodies, and the antibodies may be in the form of an antiserum comprising the antibodies. The antibodies may be of any class, such as IgG1, IgG2, IgG3, IgG4, IgM, IgA1, IgA2, IgD or IgE. The antibodies may be isolated antibodies, purified antibodies, exogenous antibodies, endogenous antibodies, or a combination thereof.

The antibodies may also be antibody fragments of less than the entire antibody, including, but not limited to, single chain antibodies, F(ab')₂ fragments, Fab fragments, and fragments produced by an Fab expression library, with the only limitation being that the antibody fragments retain the ability to bind the $\beta_1$ subunit and agonize NKA. It will thus be clear to the skilled artisan that all references to "antibodies" herein include both full-size antibodies as well as antibody fragments, as defined herein.

The antibodies may be produced in any species of animal, though preferably from a mammal such as a human, simian, mouse, rat, rabbit, guinea pig, horse, cow, sheep, goat, pig, dog or cat. For example, the antibodies can be human antibodies or humanized antibodies, or any antibody preparation suitable for administration to a human. For the production of the antibodies, the selected species of animal can be immunized by injection with one or more of the peptides or variants discussed herein. The peptides and variants may be administered in conjunction with one or more pharmaceutically acceptable adjuvants to increase the immunological response. Suitable adjuvants include, but are not limited to, Freund's Complete and Incomplete Adjuvant, Titermax, Oil in Water Adjuvants, as well as Aluminum compounds where antigens, normally peptides, are physically precipitated with hydrated insoluble salts of aluminum hydroxide or aluminum phosphate. Other adjuvants include liposome-type adjuvants comprising spheres having phospholipid bilayers that form an aqueous compartment containing the peptide and protect it from rapid degradation, and that provide a depot effect for sustained release. Surface active agents may also be used as adjuvants and include lipoteichoic acid of gram-positive organisms, lipid A, and TDM. Quil A and QS-21 (saponin-type adjuvants), monophosphoryl lipid A, and lipophilic MDP derivatives are suitable adjuvants that have hydrophilic and hydrophobic domains from which their surface-active properties arise. Compounds normally found in the body such as vitamin A and E, and lysolecithin may also be used as surface-active agents. Other classes of adjuvants include glycan analog, coenzyme Q, amphotericin B, dimethyldioctadecylammonium bromide (DDA), levamisole, and benzimidazole compounds. The immunostimulation provided by a surface active agent may also be accomplished by either developing a fusion protein with non-active portions of the cholera toxin, exotoxin A, or the heat labile toxin from *E. coli*. Immunomodulation through the use of anti-IL-17, anti IFN-γ, anti-IL-12, IL-2, IL-10, or IL-4 may also be used to promote a strong Th2 or antibody mediated response to the immunogenic formulation.

Means for preparing antibodies are very well known in the art. The antibodies of the invention can be prepared using any known technique that provides for the production of antibody molecules. Suitable techniques include, but are not limited to, the hybridoma technique originally described by Koehler and Milstein (Nature 256:495-497 (1975)), the human B-cell hybridoma technique (Kosbor et al., Immunol Today 4:72 (1983); Cote et al., Proc Natl. Acad. Sci 80:2026-2030 (1983)), and the EBV-hybridoma technique (Cole et al., Monoclonal Antibodies and Cancer Therapy, Alan R. Liss Inc, New York N.Y., pp 77-96 (1985)). Each of these publications is herein incorporated by reference in its entirety. Additionally, antibodies can be produced by inducing in vivo production in the lymphocyte population or by screening recombinant immunoglobulin libraries or panels of highly specific binding reagents as disclosed in Orlandi et al., *Proc Natl. Acad. Sci. USA* 86: 3833-3837 (1989), and in Winter G. and Milstein C., *Nature* 349:293-299 (1991), both of which is herein incorporated by reference in its entirety.

Humanized antibodies are those where a human antibody has been engineered to contain non-human complementarity-determining regions (CDRs) derived from an antibody produced in a non-human host against a selected antigen. Means for producing humanized antibodies are well-known in the art and include Vaswani S K, and Hamilton R G, *Ann Allergy Asthma Immunol.* 81(2):105-15 (1998) and Kashmiri S V et al., *Methods* 36 (1):25-34 (2005), each of which is herein incorporated by reference in its entirety.

Chimeric antibodies are those where an antigen binding region (e.g., F(ab')$_2$ or hypervariable region) of a non-human antibody is transferred into the framework of a human antibody by recombinant DNA techniques. Techniques developed for the production of such antibodies include the splicing of mouse antibody genes to human antibody genes to obtain a molecule with appropriate antigen specificity and biological activity. Such techniques are also well known and include: Morrison et al., *Proc Natl. Acad. Sci* 81:6851-6855 (1984); Neuberger et al., *Nature* 312:604-608(1984); Takeda et al., *Nature* 314:452-454(1985), each of which is herein incorporated by reference in its entirety.

Techniques for the production of single chain antibodies are described in U.S. Pat. No. 4,946,778, incorporated herein by reference in its entirety.

Antibody fragments such as F(ab')$_2$ fragments can be produced by pepsin digestion of the antibody molecule, and Fab fragments can be generated by reducing the disulfide bridges of the F(ab')$_2$ fragments. Alternatively, Fab expression libraries can be constructed to allow rapid and easy identification of monoclonal Fab fragments with the desired specificity (Huse W. D. et al., Science 256:1275-1281 (1989), herein incorporated by reference in its entirety).

As described in the Examples herein, two antibodies have been prepared that specifically bind the $\beta_1$ subunit of NKA and that also function as agonists of NKA. These antibodies are antibody JY2948 and antibody JY421228. Antibody JY2948 binds to amino acids 134-146 of the rat $\beta_1$ subunit of NKA (KERGEFNHERGER; SEQ ID NO:1) and to amino acids 134-146 of the human $\beta_1$ subunit of NKA (KERGDFNHERGER; SEQ ID NO:2). Antibody JY421228 binds to amino acids 218-230 of the rat $\beta_1$ subunit of NKA (RDEDKDKVGNIEY; SEQ ID NO:3) and to amino acids 217-229 of the human $\beta_1$ subunit of NKA (RDEDKDKVGNVEY; SEQ ID NO:4). The invention therefore provides antibody JY2948 and antibody JY421228.

The invention also provides antibodies that specifically bind an epitope of the $\beta_1$ subunit of NKA comprising the amino acid sequence KERGEFNHERGER (SEQ ID NO: 1; Rat JY2948 epitope), KERGDFNHERGER (SEQ ID NO:2; Human JY2948 epitope), KERGEFNNERGER (SEQ ID NO:5; Dog JY2948 epitope), KERGEYNNERGER (SEQ ID NO:6; Pig JY2948 epitope), or any combination thereof. Each of the antibodies has NKA agonizing activity.

The invention further provides antibodies that specifically bind an epitope of the $\beta_1$ subunit of NKA comprising the amino acid sequence RDEDKDKVGNIEY (SEQ ID NO:3; Rat JY421228 epitope) or RDEDKDKVGNVEY (SEQ ID NO:4; Human JY421228 epitope), or both. Each of the antibodies has NKA agonizing activity.

In addition, the invention provides antibodies that specifically bind the $\beta_1$ subunit of NKA and that have NKA agonizing activity.

The invention provides pharmaceutical formulations comprising one or more of the antibodies of the invention and a pharmaceutically acceptable carrier. Such formulations may be administered to a subject, such as a human, for the treatment of a disease or condition where an increase in NKA activity is desired (passive immunization). Suitable examples of carriers are well known to those skilled in the art and include water, water-for-injection, saline, buffered saline, dextrose, glycerol, ethanol, propylene glycol, polysorbate 80 (Tween-80™), poly(ethylene)glycol 300 and 400 (PEG 300 and 400), PEGylated castor oil (e.g. Cremophor EL), poloxamer 407 and 188, hydrophilic and hydrophobic carriers, and combinations thereof. Hydrophobic carriers include, for example, fat emulsions, lipids, PEGylated phospholipids, polymer matrices, biocompatible polymers, lipospheres, vesicles, particles, and liposomes. The terms specifically exclude cell culture medium. The formulations may further comprise stabilizing agents, buffers, antioxidants and preservatives, tonicity agents, bulking agents, emulsifiers, suspending or viscosity agents, inert diluents, fillers, and combinations thereof.

The identity of the carrier(s) will also depend on the means used to administer pharmaceutical formulations comprising antibodies to a subject. For example, pharmaceutical formulations for intramuscular preparations can be prepared where the carrier is water-for-injection, 0.9% saline, or 5% glucose solution. Pharmaceutical formulations may also be prepared as liquid or powdered atomized dispersions for delivery by inhalation. Such dispersion typically contain carriers common for atomized or aerosolized dispersions, such as buffered saline and/or other compounds well known to those of skill in the art. The delivery of the pharmaceutical formulations via inhalation has the effect of rapidly dispersing the vaccine formulation to a large area of mucosal tissues as well as quick absorption by the blood for circulation. One example of a method of preparing an atomized dispersion is described in U.S. Pat. No. 6,187,344, entitled, "Powdered Pharmaceutical Formulations Having Improved Dispersibility," which is hereby incorporated by reference in its entirety.

Additionally, the pharmaceutical formulations may also be administered in a liquid form. The liquid can be for oral dosage, for ophthalmic or nasal dosage as drops, or for use as an enema or douche. When the pharmaceutical formulation is formulated as a liquid, the liquid can be either a solution or a suspension of the pharmaceutical formulation. There is a variety of suitable formulations for the solution or suspension of the pharmaceutical formulations that are well known to those of skill in the art, depending on the intended use thereof. Liquid formulations for oral administration prepared in water or other aqueous vehicles may contain various suspending agents such as methylcellulose, alginates, tragacanth, pectin, kelgin, carrageenan, acacia, polyvinylpyrrolidone, and polyvinyl alcohol. The liquid formulations may also include solutions, emulsions, syrups and elixirs containing, together with the active compound(s), wetting agents, sweeteners, and coloring and flavoring agents.

Peptides

The invention also provides peptides derived from the $\beta_1$ subunit of NKA. In particular, the invention provides a peptide consisting of amino acids 134-146 of the rat $\beta_1$ subunit of NKA (KERGEFNHERGER; SEQ ID NO:1), a peptide consisting of amino acids 134-146 of the human $\beta_1$ subunit of NKA (KERGDFNHERGER; SEQ ID NO:2), a peptide consisting of amino acids 134-146 of the dog $\beta_1$ subunit of NKA (KERGEFNNERGER; SEQ ID NO:5), a peptide consisting of amino acids 134-146 of the pig $\beta_1$ subunit of NKA (KERGEYNNERGER; SEQ ID NO:6), a peptide consisting of amino acids 218-230 of the rat $\beta_1$ subunit of NKA (RDEDKDKVGNIEY; SEQ ID NO:3), and a peptide consisting of amino acids 217-229 of the human $\beta_1$ subunit of NKA (RDEDKDKVGNVEY; SEQ ID NO:4).

The invention further provides variants of each of the peptides of SEQ ID NOs:1-4. The variants having 5 or fewer, 4 or fewer, 3 or fewer, 2 or fewer, or 1 amino acid change in comparison to the peptides of SEQ ID NOs:1-4. The changes are each individually selected from insertions, deletions and substitutions. The substitutions may be conservative or non-conservative amino acid substitutions. Each of the variant peptides maintains the ability to induce production of antibodies that specifically bind the $\beta_1$ subunit of NKA and that have NKA agonist activity.

The invention provides immunogenic formulations comprising one or more of the peptides of SEQ ID NOs:1-4 and a pharmaceutically acceptable carrier and/or adjuvant. Thus, in one aspect the invention provides an immunogenic formulation comprising 1, 2, 3 or 4 of the peptides of SEQ ID NOs:1-4 and a pharmaceutically acceptable carrier and/or adjuvant. Exemplary formulations include, but are not limited to, formulations comprising SEQ ID NO:1, SEQ ID NO:2, SEQ ID NO:3, SEQ ID NO:4, SEQ ID NOs:1 and 2, SEQ ID NOs:2 and 3, SEQ ID NOs:3 and 4, SEQ ID NOs:1 and 4, SEQ ID NOs:1, 2 and 3, SEQ ID NOs:2, 3 and 4, SEQ ID NOs:1, 2 and 4, SEQ ID NOs:1, 3 and 4, or SEQ ID NOs:1, 2, 3 and 4.

The invention also provides immunogenic formulations comprising one or more variants of the peptides of SEQ ID NOs:1-4 and a pharmaceutically acceptable carrier and/or adjuvant. The invention further provides immunogenic formulations comprising (i) one or more of the peptides of SEQ ID NOs:1-4, (ii) one or more variants of the peptides of SEQ ID NOs:1-4, and (iii) a pharmaceutically acceptable carrier and/or adjuvant.

The peptides, variants and immunogenic formulations can be used in the production of antibodies having the characteristics of those disclosed herein. When used in the production of antibodies, the peptides and variants can be administered directly to an animal as described above, or administered in the context of an immunogenic formulation. The antibodies of the present invention can therefore be prepared by using one or more of the peptides of SEQ ID NOs:1-4 as an antigen, preferably in the context of an immunogenic formulation. Similarly, antibodies of the present invention can be prepared by using one or more of the peptides variants as an antigen, preferably in the context of an immunogenic formulation. The skilled artisan will understand, however, that when used as an antigen to induce antibody production, the peptides and variants, whether in the context of an immunogenic formulation or alone, need not be limited to peptides of 13 amino acids in length. Additional amino acids may be included on the amino-terminus or carboxy-terminus, or both, of the peptide or variant. Thus, 1, 2, 3, 4, 5, 6, 7, 8, 9 or more amino acids may be added to the amino-terminus or carboxy-terminus, or both, of the peptide or variant where the peptide or variant is to be administered to a host as an antigen to induce the production of anti-$\beta_1$ subunit antibodies.

As will be described in detail below, the peptides, variants and immunogenic formulations of the invention can be used to induce production of NKA $\beta_1$ subunit-binding antibodies in a subject (active immunization). When the subject is a non-human animal, antibodies can be collected after immunization, processed appropriately, and then used in methods of treatment or prevention in humans. Alternatively, the peptides, variants and immunogenic formulations of the invention can be administered directly to a human subject or non-human subject to induce endogenous production of therapeutic or protective NKA $\beta_1$ subunit-binding antibodies. The peptides, variants and immunogenic formulations can therefore be used in the treatment of a subject suffering from or susceptible to heart disease and/or a myocyte contractile disorder, or in the prevention of such diseases or disorders in the subject.

Pharmaceutically acceptable carriers and adjuvants are as described above.

Vectors

As discussed above, the peptides and variants that are used to induce production of anti-$\beta_1$ subunit antibodies can be administered directly to a subject, either "naked" or in the context of an immunogenic formulation. In addition, expression vectors encoding the peptides and variants may be administered to the subject, whereupon the encoded peptides and variants are produced, which in turn act as antigens to induce production of anti-$\beta_1$ subunit antibodies.

Thus, the invention also provides expression vectors encoding one or more of the peptides of SEQ ID NOs:1-4 and/or one or more peptide variants. Exemplary expression vectors include, but are not limited to, expression vectors encoding SEQ ID NO:1, SEQ ID NO:2, SEQ ID NO:3, SEQ ID NO:4, SEQ ID NOs:1 and 2, SEQ ID NOs:2 and 3, SEQ ID NOs:3 and 4, SEQ ID NOs:1 and 4, SEQ ID NOs:1, 2 and 3, SEQ ID NOs:2, 3 and 4, SEQ ID NOs:1, 2 and 4, SEQ ID NOs:1, 3 and 4, or SEQ ID NOs:1, 2, 3 and 4. Other exemplary expression vectors include, but are not limited to, expression vectors encoding 1, 2, 3, 4 or more variants. When a single expression vector encodes more than one peptide or variant, the coding regions are arranged in 5' to 3' alignment on the vector with suitable spacing between the different coding regions.

In certain aspects, the vectors are under the control of tissue specific promoters including, but not limited to, cardiac tissue specific promoters or other appropriate tissue-specific promoters.

The invention further provides pharmaceutical formulations comprising one or more of the vectors and a pharmaceutically acceptable carrier. In one aspect the invention provides a pharmaceutical formulations comprising expression vectors encoding 1, 2, 3 or 4 of the peptides of SEQ ID NOs:1-4 and a pharmaceutically acceptable carrier. Exemplary formulations include, but are not limited to, formulation comprising expression vectors encoding SEQ ID NO:1, SEQ ID NO:2, SEQ ID NO:3, SEQ ID NO:4, SEQ ID NOs:1 and 2, SEQ ID NOs:2 and 3, SEQ ID NOs:3 and 4, SEQ ID NOs:1 and 4, SEQ ID NOs:1, 2 and 3, SEQ ID NOs:2, 3 and 4, SEQ ID NOs:1, 2 and 4, SEQ ID NOs:1, 3 and 4, or SEQ ID NOs:1, 2, 3 and 4. Other exemplary formulations include, but are not limited to, formulation comprising expression vectors encoding 1, 2, 3, 4 or more variants.

The skilled artisan will understand that there is a wide variety of expression vector combinations that may make up the pharmaceutical formulations. For example, a pharmaceutical formulation may be prepared where all of the expression vectors therein have the same nucleotide sequence. As an illustration, the vector may encode only one of the peptides of SEQ ID NOs:1-4, or the same vector may encode two, three or all four of the peptides, arranged in 5' to 3' alignment on the vector with suitable spacing between the different coding regions. Alternatively, a pharmaceutical formulation may be prepared comprise expression vectors of two or more different sequences. As an illustration, vector A of the formulation may encode one of the peptides of SEQ ID NOs:1-4, while vector B of the formulation encodes one of the other peptides. Additional pharmaceutical formulation can be readily envisioned that comprise vectors encoding one peptide and vectors encoding two or more peptides.

Pharmaceutically acceptable carriers are as described above.

As will be described in detail below, the vectors and pharmaceutical formulations comprising the vectors can be used to induce production of NKA $\beta_1$ subunit-binding antibodies in a subject, which in turn can be used in methods of treatment or prevention in the subject. The vectors and pharmaceutical formulations can therefore be used in the treatment of a subject suffering from or susceptible to heart disease and/or a myocyte contractile disorder, or in the prevention of such diseases or disorders in the subject.

Methods

In conjunction with the NKA agonist activity exhibited by the anti-$\beta_1$ subunit antibodies of the invention, also provided are methods for increasing NKA activity comprising contacting the $\beta_1$ subunit of NKA with an antibody that specifically binds an epitope of the $\beta_1$ subunit and that has NKA agonist activity. The contacting may be in vitro, such as in experiments conducted to determine the effects of a test compound on the activity of NKA, or in vivo, such as in efforts to increase NKA activity in a subject. The antibodies that may be used in this method include any of the antibodies described herein, such as an antibody that specifically binds one or more of the peptides represented by SEQ ID NOs:1-4, antibody JY421228, or antibody JY2948.

The invention provides methods for inducing and/or increasing cardiac myocyte contraction comprising contacting a cardiac myocyte with an antibody that specifically binds an epitope of the $\beta_1$ subunit of NKA and that has NKA agonist activity. The contacting may be in vitro, such as in experiments conducted to determine the effects of a test compound on cardiac myocyte contraction, or in vivo, such as in efforts to increase cardiac myocyte contraction in a subject. The antibodies that may be used in this method include any of the antibodies described herein, such as an antibody that specifically binds one or more of the peptides represented by SEQ ID NOs:1-4, antibody JY421228, or antibody JY2948.

The invention provides methods for inhibiting cardiac hypertrophy comprising contacting a heart with an antibody that specifically binds an epitope of the $\beta_1$ subunit of NKA and that has NKA agonist activity. The contacting may be in vitro, such as in experiments conducted to determine the effects of a test compound on inhibiting cardiac hypertrophy, or in vivo, such as in efforts to inhibit cardiac hypertrophy in a subject. The antibodies that may be used in this method include any of the antibodies described herein, such as an antibody that specifically binds one or more of the peptides represented by SEQ ID NOs:1-4, antibody JY421228, or antibody JY2948.

The invention provides methods for inducing and/or increasing cardiac contraction comprising contacting a heart with an antibody that specifically binds an epitope of the $\beta_1$ subunit of NKA and that has NKA agonist activity. The contacting may be in vitro, such as in experiments conducted to determine the effects of a test compound on cardiac contraction, or in vivo, such as in efforts to increase cardiac contraction in a subject. The antibodies that may be used in this method include any of the antibodies described herein, such as an antibody that specifically binds one or more of the peptides represented by SEQ ID NOs:1-4, antibody JY421228, or antibody JY2948.

The invention provides methods for increase the force of cardiac contraction comprising contacting a heart with an antibody that specifically binds an epitope of the $\beta_1$ subunit of NKA and that has NKA agonist activity. The contacting may be in vitro, such as in experiments conducted to determine the effects of a test compound on increasing the force of cardiac contraction, or in vivo, such as in efforts to increase the force of cardiac contraction in a subject. The antibodies that may be used in this method include any of the antibodies described herein, such as an antibody that specifically binds one or more of the peptides represented by SEQ ID NOs:1-4, antibody JY421228, or antibody JY2948.

The invention provides methods for inducing an immune response in a subject, comprising administering to a subject an immunologically effective amount of an immunogenic formulation comprising (i) one or more peptides of SEQ ID NOs:1-4, and/or variants thereof, and (ii) a pharmaceutically acceptable carrier and/or adjuvant. Exemplary formulations include, but are not limited to, formulations comprising SEQ ID NO:1, SEQ ID NO:2, SEQ ID NO:3, SEQ ID NO:4, SEQ ID NOs:1 and 2, SEQ ID NOs:2 and 3, SEQ ID NOs:3 and 4, SEQ ID NOs:1 and 4, SEQ ID NOs:1, 2 and 3, SEQ ID NOs:2, 3 and 4, SEQ ID NOs:1, 2 and 4, SEQ ID NOs:1, 3 and 4, or SEQ ID NOs:1, 2, 3 and 4. Other exemplary formulations include, but are not limited to, formulations comprising 1, 2, 3, 4 or more variants. Pharmaceutically acceptable carriers and adjuvants are as described above.

Methods of Treatment

The invention also provides methods for treating or preventing particular diseases, disorders and conditions in a subject by increasing NKA activity through the administration of peptides or variants that induce production of anti-$\beta_1$ subunit antibodies or direct administration of such antibodies.

Thus, the invention provides methods for treating a disease in a subject, comprising administering to a subject in need of treatment a pharmaceutical formulation comprising (i) one or more antibodies that specifically binds the $\beta_1$ subunit of NKA and having NKA agonist activity and (ii) a pharmaceutically acceptable carrier, thereby treating heart disease in a subject. The antibodies that may be used in this method include any of the antibodies described herein, such as an antibody that specifically binds one or more of the peptides represented by SEQ ID NOs:1-4, antibody JY421228, or antibody JY2948. Pharmaceutically acceptable carriers are as described above.

The invention also provides methods for treating a disease in a subject, comprising administering to a subject in need of treatment an immunogenic formulation comprising (i) one or more peptides of SEQ ID NOs:1-4, and/or variants thereof, and (ii) a pharmaceutically acceptable carrier and/or adjuvant, wherein the immunogenic formulation induces endogenous production of an antibody that specifically binds the $\beta_1$ subunit of Na$^+$/K$^+$ ATPase (NKA) and that has NKA agonizing activity, thereby treating heart disease in a subject. Exemplary formulations include, but are not limited to, formulations comprising SEQ ID NO:1, SEQ ID NO:2, SEQ ID NO:3, SEQ ID NO:4, SEQ ID NOs:1 and 2, SEQ ID NOs:2 and 3, SEQ ID NOs:3 and 4, SEQ ID NOs:1 and 4, SEQ ID NOs:1, 2 and 3, SEQ ID NOs:2, 3 and 4, SEQ ID NOs:1, 2 and 4, SEQ ID NOs:1, 3 and 4, or SEQ ID NOs:1, 2, 3 and 4. Other exemplary formulations include, but are not limited to, formulations comprising 1, 2, 3, 4 or more variants. Pharmaceutically acceptable carriers and adjuvants are as described above.

The invention further provides methods for treating a disease in a subject, comprising administering to a subject in need of treatment a pharmaceutical formulation comprising (i) one or more vectors encoding one or more peptides SEQ ID NOs:1-4, and/or variants thereof, and (ii) a pharmaceutically acceptable carrier, wherein the one or more peptides and/or variants are produced in the subject, followed by induction of endogenous production of an antibody that specifically binds the $\beta_1$ subunit of Na$^+$/K$^+$ ATPase (NKA) and that has NKA agonizing activity, thereby treating heart disease in a subject. Exemplary formulations include, but are not limited to, formulation comprising expression vectors encoding SEQ ID NO:1, SEQ ID NO:2, SEQ ID NO:3, SEQ ID NO:4, SEQ ID NOs:1 and 2, SEQ ID NOs:2 and 3, SEQ ID NOs:3 and 4, SEQ ID NOs:1 and 4, SEQ ID NOs:1, 2 and 3, SEQ ID NOs:2, 3 and 4, SEQ ID NOs:1, 2 and 4, SEQ ID NOs:1, 3 and 4, or SEQ ID NOs:1, 2, 3 and 4. Other exemplary formulations include, but are not limited to, formulation comprising expression vectors encoding 1, 2, 3, 4 or more variants. Pharmaceutically acceptable carriers are as described above.

In each of the methods of treatment, the disease is one or more diseases selected from the group consisting of diabetes, lung diseases, liver diseases, urinary tract diseases, hemorrhagic shock, gastrointestinal diseases including colitis, cataracts, hypertension, Alzheimer's disease, eye disease, heart disease, myocyte contractile disorder, aging, cancer, kidney diseases, obesity and diseases of the nervous system. In one aspect the disease is heart disease. In another aspect the disease is myocyte contractile disorder, in which the cardiac myocytes cannot contract as strongly as needed to maintain good health. For example, the ability of the heart to contract can be compromised by diseases or events such as myocardial infarction (i.e., heart attack), infection of the heart (myocarditis), exposure of the heart to toxins that impair its function (such as a chemotherapeutic agents or excessive alcohol use), and the like.

As used herein, the terms "treat", "treating" and "treatment" have their ordinary and customary meanings, and include one or more of, ameliorating a symptom of a disease, blocking or ameliorating a recurrence of a symptom of a disease, decreasing in severity and/or frequency a symptom of a disease. Treatment means ameliorating, blocking, reducing, decreasing or inhibiting by about 1% to about 100% versus a subject to which the treatment has not been administered. Preferably, the ameliorating, blocking, reducing, decreasing or inhibiting is about 100%, about 99%, about 98%, about 97%, about 96%, about 95%, about 90%, about 80%, about 70%, about 60%, about 50%, about 40%, about 30%, about 20%, about 10%, about 5% or about 1%. The treatment may begin prior to, concurrent with, or after the onset of clinical symptoms of the disease. Thus, the subject may have a disease or merely be susceptible to the disease. The results of the treatment may be permanent or may continue for a period of days (such as 1, 2, 3, 4, 5, 6 or 7 days), weeks (such as 1, 2, 3 or 4 weeks) or months (such as 1, 2, 3, 4, 5, 6 or more months).

The invention provides methods for preventing a disease in a subject, comprising administering to a subject in need of prevention a pharmaceutical formulation comprising (i) one or more antibodies that specifically binds the $\beta_1$ subunit of NKA and having NKA agonist activity and (ii) a pharmaceutically acceptable carrier, thereby preventing heart disease in a subject. The antibodies that may be used in this method include any of the antibodies described herein, such as an antibody that specifically binds one or more of the peptides represented by SEQ ID NOs:1-4, antibody JY421228, or antibody JY2948. Pharmaceutically acceptable carriers are as described above.

The invention also provides methods for preventing a disease in a subject, comprising administering to a subject in need of prevention an immunogenic formulation comprising (i) one or more peptides of SEQ ID NOs:1-4, and/or variants thereof, and (ii) a pharmaceutically acceptable carrier and/or adjuvant, wherein the immunogenic formulation induces endogenous production of an antibody that specifically binds the β₁ subunit of Na⁺/K⁺ ATPase (NKA) and that has NKA agonizing activity, thereby preventing heart disease in a subject. Exemplary formulations include, but are not limited to, formulations comprising SEQ ID NO:1, SEQ ID NO:2, SEQ ID NO:3, SEQ ID NO:4, SEQ ID NOs:1 and 2, SEQ ID NOs:2 and 3, SEQ ID NOs:3 and 4, SEQ ID NOs:1 and 4, SEQ ID NOs:1, 2 and 3, SEQ ID NOs:2, 3 and 4, SEQ ID NOs:1, 2 and 4, SEQ ID NOs:1, 3 and 4, or SEQ ID NOs:1, 2, 3 and 4. Other exemplary formulations include, but are not limited to, formulations comprising 1, 2, 3, 4 or more variants. Pharmaceutically acceptable carriers and adjuvants are as described above.

The invention further provides methods for preventing a disease in a subject, comprising administering to a subject in need of prevention a pharmaceutical formulation comprising (i) one or more vectors encoding one or more peptides SEQ ID NOs:1-4, and/or variants thereof, and (ii) a pharmaceutically acceptable carrier, wherein the one or more peptides and/or variants are produced in the subject, followed by induction of endogenous production of an antibody that specifically binds the β₁ subunit of Na⁺/K⁺ ATPase (NKA) and that has NKA agonizing activity, thereby preventing heart disease in a subject. Exemplary formulations include, but are not limited to, formulation comprising expression vectors encoding SEQ ID NO:1, SEQ ID NO:2, SEQ ID NO:3, SEQ ID NO:4, SEQ ID NOs:1 and 2, SEQ ID NOs:2 and 3, SEQ ID NOs:3 and 4, SEQ ID NOs:1 and 4, SEQ ID NOs:1, 2 and 3, SEQ ID NOs:2, 3 and 4, SEQ ID NOs:1, 2 and 4, SEQ ID NOs:1, 3 and 4, or SEQ ID NOs:1, 2, 3 and 4. Other exemplary formulations include, but are not limited to, formulation comprising expression vectors encoding 1, 2, 3, 4 or more variants. Pharmaceutically acceptable carriers are as described above.

In each of the methods of prevention, the disease is one or more diseases selected from the group consisting of diabetes, lung diseases, liver diseases, urinary tract diseases, hemorrhagic shock, gastrointestinal diseases including colitis, cataracts, hypertension, Alzheimer's disease, eye disease, heart disease, myocyte contractile disorder, aging, cancer, kidney diseases, obesity and diseases of the nervous system. In one aspect the disease is heart disease. In another aspect the disease is myocyte contractile disorder.

As used herein, the terms "prevent", "preventing" and "prevention" have their ordinary and customary meanings, and include one or more of, stopping, averting, avoiding, alleviating or blocking the occurrence of a symptom of a disease, the recurrence of a symptom of a disease, the development of a disease or the progression of a disease. Prevention means stopping by at least about 95% versus a subject to which the prevention has not been administered. Preferably, the stopping is about 100%, about 99%, about 98%, about 97%, about 96% or about 95%. The course of therapy may begin prior to, concurrent with, or after the onset of clinical symptoms of the disease. Thus, the subject may have a disease or merely be susceptible to the disease. The results of the prevention may be permanent or may continue for a period of days (such as 1, 2, 3, 4, 5, 6 or 7 days), weeks (such as 1, 2, 3 or 4 weeks) or months (such as 1, 2, 3, 4, 5, 6 or more months).

In each of the methods of treatment and prevention of the present invention the immunogenic formulations comprising one or more peptides of SEQ ID NOs:1-4, and/or variants thereof, are administered in a pharmaceutically acceptable form and in substantially non-toxic quantities. The immunogenic formulations may be administered to a subject using different immunization schedules, depending on the particular disease being treated or prevented, and severity thereof; the age and size of the subject; and the general health of the subject, to name only a few factors to be considered. In general, the immunogenic formulations may be administered once, or twice, three times, four times, five times, six times or more, over a course of treatment or prevention. The timing between each dose in a dosing schedule may range between days, weeks, months, or years, an includes administered once every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more weeks. The same quantity of protein in the formulation may be administered in each dose of the dosing schedule, or the amounts in each dose may vary. The identity of the particular peptides and variants in the formulation may also vary or remain the same in each dose in a dosing schedule.

The amount of the peptide and/or variant administered to a subject in a dose when the methods of the present invention are practiced will again vary. However, the amount administered to a subject in a dose will be sufficient to induce or boost an immune response in a subject to the components of the immunogenic formulation. As an example, a therapeutically effective amount of peptide and/or variant in a dose of a immunogenic formulation of the present invention is typically between about 10 to about 200 ug of protein per kg of body weight of the subject to which the dose of the immunogenic formulation is be administered.

Appropriate doses and dosing schedules can readily be determined by techniques well known to those of ordinary skill in the art without undue experimentation. Such a determination will be based, in part, on the tolerability and efficacy of a particular dose.

Administration of the immunogenic formulations may be via any of the means commonly known in the art of vaccine delivery. Such routes include intravenous, intraperitoneal, intramuscular, subcutaneous and intradermal routes of administration, as well as nasal application, by inhalation, ophthalmically, orally, rectally, vaginally, or by any other mode that results in the vaccine formulation contacting mucosal tissues.

Each of the methods of the present invention may also be practiced whereby an additional therapeutic agent is administered to the subject, in addition to the peptides, vectors and antibodies described herein. Such additional therapeutic agents will generally be those that are also known to have a therapeutic effect on the disease, disorder or condition being treated. Suitable additional therapeutic agents for use in the treatment of heart disease, for example, include diuretics, digoxin, AVE inhibitors, beta blockers and anti-NKA alpha subunit antibodies (as described in U.S. Pat. No. 7,754,210, the entire disclosure of which is herein incorporated by reference in its entirety).

The term "subject" is intended to mean an animal, such birds or mammals, including humans and animals of veterinary or agricultural importance, such as dogs, cats, horses, sheep, goats, and cattle.

A kit comprising the necessary components for active immunization, including an immunogenic formulation comprising a peptide that elicits an immune response and instructions for its use, is also within the purview of the present invention. In addition, a kit comprising the necessary components for passive immunization, including a pharmaceutical formulation comprising an antibody that induces cardiac contraction and instructions for its use, is within the purview of the present invention.

It is understood that the examples and embodiments described herein are for illustrative purposes only and that various modifications or changes in light thereof will be suggested to persons skilled in the art and are to be included within the spirit and purview of this application and scope of the appended claims.

All documents, papers and published materials referenced herein, including books, journal articles, manuals, patent applications, published patent applications and patents, are expressly incorporated herein by reference in their entireties.

EXAMPLES

Antibody JY2948
Materials and Methods
Materials.

Cell permeable Sodium Green tetraacetate was purchased from Molecular Probes (Eugene, Oreg.). Nifedipine and KB-R7943 were from Tocris (Ellisville, Mo.). Calcium-45 with a concentration of 37.92 mCi/ml was from PerkinElmer (Boston, Mass.). Sprague Dawley rats were from Charles River (Germantown, Md.). Dog kidney tissues were gifts from Dr. Jack Kyte's laboratory (University of California, San Diego, USA). SDS-stripped pig $\alpha_1$ and $\beta_1$ subunits were gifts from Dr. Osamu Urayama (University of Tsukuba, Japan).

Antibody Preparation.

The KERGEFNHERGER peptide (rat NKA $\beta_1$ sequence; SEQ ID NO:1) was synthesized by BioSynthesis (Lewisville, Tex.) as an antigen and monoclonal antibody JY2948 was generated by CytoMol Corp. (Union City, Calif.). The immunoglobulins (IgG) were further purified through a peptide affinity column directed against the same synthetic peptide antigen. The synthetic peptide was also utilized as specific peptide blocker (PB2948) for the JY2948 antibody.

NKA Preparation.

Membrane-bound rat cardiac NKA and dog kidney NKA were purified and enzymatic activity was determined by the method of Kyte (17). The specific enzymatic activity in these preparations was between 230 and 420 $\mu$mol mg$^{-1}$ h$^{-1}$ for rat NKA and between 980 and 1590 $\mu$mol mg$^{-1}$ h$^{-1}$ for dog kidney NKA.

Isolation of Cardiac Myocytes and Measurement of Cell Contraction.

Rat ventricular myocytes were isolated as described (18). The contraction amplitude was indexed by the percentage shortening of cell length (19).

Immunofluorescent Staining.

Isolated rat cardiac myocytes were frozen and cross sections cut on a cryostat. Sections (8 $\mu$m) of each tissue were blocked with 1% bovine serum albumin (BSA) and incubated with JY2948 (1:1000) for 60 min in the presence or absence of 1 mM PB2948. Washed slides were evaluated after incubation with a FITC-conjugated goat anti-mouse antibody (1:75).

Analyses of Enzyme Kinetic Parameters.

Ouabain-sensitive enzymatic activity of both rat and dog NKA were measured based on the method of Jack Kyte (17) with modifications as described previously (19) in 10 mM Tris/HCl buffer at pH 7.4 under various experimental conditions. JY2948 was incubated with NKA at room temperature for 60 min, allowing maximum JY2948 antibody binding to the enzyme prior to initiating ATP hydrolysis. Reactions were performed at 37° C. for 30 min in the presence or absence of different concentrations of ouabain (1 mM for dog NKA and 2.5 mM for rat NKA). The concentrations of phosphate were determined at 700 nm using a spectrophotometer (19). To determine the apparent EC$_{50}$ of JY2948, NKA activity was measured in Tris buffer containing 100 mM Na$^+$, 20 mM K$^+$, and 3 mM MgATP with different concentrations of JY2948 (0, 0.1, 0.3, 0.5, 1, and 2 $\mu$M). To measure the apparent Km for ATP, the media contains fixed Na$^+$ (100 mM) and K$^+$ (20 mM) with different concentrations of MgATP (0, 0.2, 0.4, 0.6, 0.8, 1, 3, and 5 mM) in the presence and absence of JY2948 (0.5 $\mu$M). To determine Na$^+$ affinity, various concentrations of Na$^+$ (0, 3, 5, 10, 20, 40, 80 and 100 mM) were applied with fixed K$^+$ (20 mM) and MgATP (3 mM) with or without JY2948 (0.5 $\mu$M). To determine K$^+$ affinity, different concentrations of K$^+$ (0, 0.3, 0.5, 1, 2, 4, 10 and 20 mM) were used with fixed Na$^+$ (100 mM) and MgATP (3 mM) in the presence and absence of JY2948 (0.5 $\mu$M). NKA turnover number ($k_{cat}$) was calculated using the equation $k_{cat}=V_{max}/E_t$, where $V_{max}$ is the maximum reaction rate and $E_t$ represents enzyme molar concentration. Kinetic parameters were analyzed by the Michaelis-Menten equation $v=V_{max}[S]/(K_m+[S])$, where S is the concentration of ATP, Na$^+$ or K$^+$, and $K_m$ (apparent affinity) represents the substrate concentration that produces exactly half the maximum reaction rate.

Western Blotting.

Samples of purified rat and dog NKA, along with SDS-stripped pig $\alpha$1 and $\beta$1 subunits (30 $\mu$g each) were mixed with electrophoresis sample buffer separately, boiled for 5 min, and loaded on freshly made 7.5% SDS-PAGE gel. Following electrophoresis, the samples were transferred from the SDS gel to a nitrocellulose membrane (0.45 $\mu$m). The nitrocellulose membranes were blocked with 5% BSA for 2 hours at room temperature (RT) and incubated overnight with different primary antibodies including SSA412 and JY2948 (1:1000) separately at 4° C. The membranes were then washed and incubated with secondary antibody (1:7500) for 1 hour. The color was then developed for visual analysis.

Nifedipine and KB-R7943 Sensitive $^{45}$Ca Influx.

$^{45}$Ca influx was performed with isolated rat myocytes in the presence and absence of JY2948 with or without 10 $\mu$M nifedipine (LTCC inhibitor) and 5 $\mu$M KB-R7943 (NCX inhibitor) in a buffer containing 137 mM NaCl, 4.9 mM KCl, 1.2 mM MgCl$_2$, 1.2 mM NaH$_2$PO$_4$, and 10 mM Hepes at pH 7.4 for 60 min at room temperature. The final concentrations of $^{45}$Ca, CaCl$_2$, JY2948, and ouabain in the reaction mixture were 20 nCi, 10 $\mu$M, 0.5 $\mu$M, and 2.5 mM. The reaction was stopped by adding 5 mM EGTA on ice and cells were washed and spun at 4000 rpm for 2 min (×3) to remove extracellular $^{45}$Ca. Net intracellular counts per minute (cpm) of $^{45}$Ca for each sample was determined by using a $\beta$-scintillation counter and the concentration of $^{45}$Ca was calculated as described previously (20).

Measurement of Sodium Green Fluorescence Emission.

Myocytes were incubated with Sodium Green tetraacetate (21) at room temperature for 60 min and washed to remove excess probe prior to addition of JY2948 (0.5 $\mu$M) or ouabain (2.5 mM). The final concentration of Sodium Green in each sample tube was 10 $\mu$M during the incubation. The myocytes were then transferred to 96-well plates (Nunc) and the measurement of Sodium Green fluorescence was carried out by excitation at 485 nm and quantifying emission at 535 nm using a VICTOR-II multilabel counter (PerkinElmer Life Sciences).

Statistics.

All data are expressed as mean±SEM. Student's t test and paired t test were applied when appropriate. A P value less than 0.01 was considered statistically significant.

Specific Interaction Between JY2948 Antibody and NKA $\beta_1$ Subunit.

To explore the potential allosteric property of NKA $\beta_1$ subunit, we first established a specific interaction with $\beta_1$ subunit. Monoclonal antibody JY2948 was generated against the $^{134}$KERGEFNHERGER$^{146}$ peptide (SEQ ID NO:1), which resides within the primary sequence of rat NKA $\beta_1$ protein and we examined the specificity of JY2948. Amino acid sequence comparison reveals that the antigenic site of JY2948 is highly conserved within NKA $\beta_1$ subunits among different species including rat, human, dog, and pig (FIG. 1A). The other isoforms of NKA $\beta$ subunits, including $\beta_2$ and $\beta_3$, do not contain such a site (data not shown). Confocal immunofluorescence image shows that JY2948 binds to $\beta_1$ subunit on the extracellular side of isolated rat cardiac myocytes (FIG. 1B, panels a and b). Western blots further demonstrate that JY2948 recognizes and interacts only with the $\beta_1$ but not the $\alpha_1$ subunit of the enzyme (FIG. 1C, lanes d, e, and f). This specific interaction between JY2948 and native $\beta_1$ subunit is completely abolished in the presence of peptide blocker PB2948 (FIG. 1C, lanes g, h and i), demonstrating the specificity of antibody JY2948.

NKA Activity Is a Function of the Concentration of JY2948.

We next investigated the impact of specific binding of JY2948 to the $\beta_1$ subunit on NKA enzymatic activity. FIG. 2 shows that the maximal activity of control NKA is a function of the concentration of JY2948. In the presence of 0, 0.1, 0.3, 0.5, 1 and 2 µM JY2948, the activity of rat NKA was 100, 134±14, 157±7.5, 169±4.2, 180±13 and 184±4.0% (FIG. 2A), and the activity of dog NKA was 100, 158±29, 230±16, 249±25, 273±17 and 273±6.4% (FIG. 2B), respectively. The half maximal effective concentration ($EC_{50}$) of JY2948, which induces a response halfway between the control NKA without JY2948 and maximum enzyme activity with JY2948, was 0.17±0.1 and 0.18±0.03 µM for rat and dog NKA, respectively. These results show that the $\beta_1$ subunit possesses allosteric activity.

JY2948 Enhances NKA Maximal Velocity ($V_{max}$) without Affecting Apparent Affinity (Km) of ATP.

Following identification of an allosteric site on the $\beta_1$ subunit, we explored the characteristics of the allosteric activity of the NKA $\beta_1$ subunit. ATP is the substrate of NKA. We next investigated whether interactions between JY2948 and $\beta_1$ subunit would affect the ATP concentration $\frac{1}{2}V_{max}$. With different concentrations of MgATP (0, 0.2, 0.4, 0.6, 0.8, 1, 3 and 5 mM) without JY2948, the control enzyme activity was 0, 22±18, 56±13, 66±14, 72±15, 79±8, 96±5 and 100% for rat NKA (FIG. 2CA), and 0, 38±12, 58±13, 65±15, 74±13, 80±7, 97±5 and 100% for dog NKA (FIG. 2D). In contrast, NKA activity was 0, 66±6, 99±26, 113±9, 129±31, 142±21, 168±40 and 185±8% (FIG. 2C) for rat, and 0, 76±12, 124±21, 165±49, 180±21, 190±14, 206±48, 215±61% for dog NKA (FIG. 2D) in the presence of 0.5 µM JY2948. $V_{max}$ was determined under the condition of ATP saturation. The $V_{max}$ values for rat and dog NKA control samples were 344±99 and 1255±252 µmol·g$^{-1}$h$^{-1}$. In the presence of 0.5 JY2948, the $V_{max}$ values were 583±22 and 3098±317 µmol·g$^{-1}$h$^{-1}$, respectively. Km values of ATP were 0.36±0.15 and 0.36±0.04 mM for rat NKA, 0.34±0.17 and 0.34±0.1 mM for dog NKA with or without JY2948. No difference was detected for Km values of ouabain-resistant rat and ouabain-sensitive dog NKA.

The JY2948-$\beta_1$ Subunit Interaction Alters Na$^+$ and K$^+$ Ion Affinity.

Hydrolysis of ATP by NKA is a Na$^+$ and K$^+$ ion dependent process. We next investigated the effect of JY2948 on Na$^+$ and K$^+$ ion affinity for NKA. With different concentrations of Na$^+$, including 0, 3, 5, 10, 20, 40, 80 and 100 mM and fixed concentration of K$^+$ (20 mM) and ATP (3 mM), the control enzyme activity was 0, 19±16, 29±20, 57±13, 78±10, 93±7.0, 98±4.0, 100% for rat NKA (FIG. 3A), and 0, 19±18, 25±17, 60±17, 77±4.0, 86±3.0, 99±2.0, 100% for dog NKA (FIG. 3B). In the presence of 0.5 µM JY2948 under the same experimental conditions, enzyme activity was increased to 0, 66±29, 120±2.0, 139±11, 162±7.0, 182±5.0, 196±14, 200±17% for rat (FIG. 3A) and 0, 70±11, 167±25, 188±25, 216±49, 230±73, 244±22, 243±11% for dog NKA (FIG. 3B). The apparent Na$^+$ affinity of the control samples were estimated to be 8.8±4.0 and 8.6±2.1 mM for rat and dog NKA, which were significantly changed to 4.2±0.3 and 4.1±0.1 mM in the presence of 0.5 µM JY2948.

Figure 4:
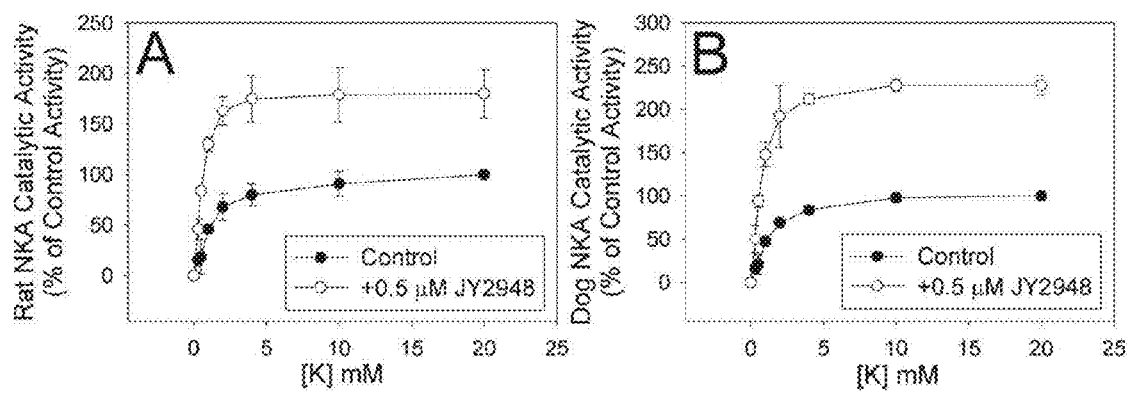
FIG. 4. Allosteric effect of β1 subunit on K$^+$ affinity of NKA. Purified rat NKA (A, 5 μg/ml) and dog (B, 0.8 μg/ml) NKA were incubated with 0.5 μM JY2948 at RT for 60 min prior to ouabain-sensitive ATPase assay in the presence of 0, 0.3, 0.5, 1, 2, 4, 10, and 20 mM K$^+$. The concentrations of Na$^+$ and ATP in the assay were 100 mM and 3 mM, respectively. Each data point represents the mean±SEM of five independent experiments. Binding of JY2948 to 131-subunit of NKA increases the NKA K$^+$ affinity.

Interactions between JY2948 and NKA $\beta_1$ subunit appear to have a similar effect on K$^+$ affinity (FIG. 4). With different concentrations of K$^+$, including 0, 0.3, 0.5, 1.0, 2.0, 4.0, 10 and 20 mM and with fixed Na$^+$ (100 mM) and ATP (3 mM), the enzyme activity of control samples were 0, 16±6.0, 18±17, 46±2.0, 68±13, 80±11, 91±12 and 100% for rat NKA (FIG. 4A), and 0, 16±4.0, 21±11, 47±2.0, 69±6.0, 84±5.0, 98±5.0 and 100% for dog NKA (FIG. 4B). In the presence of 0.5 µM JY2948 under the same experimental conditions, the enzyme activity was increased to 0, 46±10, 84±3.0, 130±7.0, 163±14, 175±23, 179±27 and 180±24% for rat (FIG. 4A), and 0, 50±16, 94±7.0, 148±14, 192±36, 212±6.0, 228±7.0 and 228±11% for dog NKA (FIG. 4B), respectively. The apparent K$^+$ affinity of control samples for rat and dog were 1.25±0.2 and 1.20±0.1 mM. These values are reduced to 0.61±0.1 and 0.65±0.1 mM in the presence of 0.5 µM JY2948, compared with the control samples, for rat and dog NKA, respectively.

Binding of JY2948 to NKA $\beta_1$ Subunit Induces Positive Inotropic Effect on Isolated Rat Myocyte.

Having determined the effect of binding of JY2948 to $\beta_1$ subunit on NKA catalytic function, we further explored whether JY2948-induced enzymatic changes would influence cardiac myocyte contractility through the a subunit of the enzyme. When 0.5 µM JY2948 binds to isolated rat myocytes, the contractility of rat myocyte was increased 2-fold (FIGS. 5A-b, B-b) compared with the control background (FIGS. 5A-a, B-a). This positive inotropic effect, induced by interaction with the NKA $\beta_1$ subunit, was completely eliminated when PB2948 (FIGS. 5A-c, B-c). No increase of contractility was detected in the presence of denatured JY2948 (FIGS. 5A-d, B-d).

Impact of JY2948-$\beta_1$ Subunit Interaction on Cellular Ca$^{2+}$ Movement.

As a ubiquitous intracellular messenger, Ca$^{2+}$ plays a critical role in cardiac contraction. To understand NKA $\beta_1$ subunit-mediated positive inotropy, we investigated the movement of Ca$^{2+}$ ions from the extracellular to the intracellular compartment in isolated rat myocytes initiated by JY2948-$\beta_1$ subunit interaction Inhibitor sensitive $^{45}$Ca influx was performed using nifedipine [inhibitor of L-type Ca$^{2+}$ channel (LTCC)] and KB-R7943 [inhibitor of Na$^+$/Ca$^{2+}$-exchanger (NCX)] (22) with or without JY2948 or ouabain. No significant changes of $^{45}$Ca concentration in the presence of 10 µM nifedipine and 5 µM KB-R7943 were detected compared with the control cell background (FIGS. 6a, b and c). However, binding of JY2948 to $\beta_1$ subunit caused a 74.9±19 pCi $^{45}$Ca influx into the cells (FIG. 6d). Nifedipine (10 µM) completely blocked JY2948-induced $^{45}$Ca influx (FIG. 6e), but 74.2±20 pCi $^{45}$Ca was detected in the cells with 5 µM KB-R7943. In contrast, ouabain induced a 330±6.4 pCi $^{45}$Ca influx (FIG. 6g). In the presence of 10 µM nifedipine and 5 µM KB-R7943, nifedipine-resistant $^{45}$Ca influx was 188±78 and 128±16 pCi for KB-R7943-resistant $^{45}$Ca influx, respectively (FIGS. 6h and i). Ouabain-induced $^{45}$Ca influx was completely impeded in the presence of both nifedipine and KB-R7943 (FIG. 6j).

Effect of JY2948-$\beta_1$ Subunit Interaction on Na$^+$ Homeostasis and NCX Function.

To understand whether the NKA $\beta_1$ subunit-mediated positive inotropic effect alters Na$^+$ homeostasis in the myocyte, we investigated and compared the impact of JY2948 and ouabain on the intracellular Na$^+$ concentration in the presence and absence of different concentrations of NCX inhibitor KB-R7943. It has been demonstrated that at low concentration of KB-R7943, it inhibits the reverse-mode of NCX; at high concentration, it inhibits forward-mode of the exchanger (22). It is our strategy to utilize these unique properties of KB-R7943 to distinguish different modes of NCX. Sodium Green fluorescence intensity was 100, 99±10, and 102±7.0% for control myocytes, or with 5 μM KB-R7943, and with 30 μM of KB-R7943, respectively (FIGS. 7a, b and c). Fluorescence intensity was 98±11% (FIG. 7d) compared with control cells (FIG. 7a) when JY2948 interacted with NKA $\beta_1$ subunit. No alteration was detected in the presence of 5 μM KB-R7943 (100±6.0%, FIG. 7e). However, fluorescence intensity was reduced to 71±18% with 30 μM of KB-R7943 (FIG. 7f) in the presence of JY2948. In contrast, ouabain caused a significant alteration in intracellular Na$^+$ concentration. The Sodium Green fluorescence intensity was 136±13, 153±19 and 151±23% for the samples with ouabain, ouabain+5 μM KB-R7943, and ouabain+30 μM KB-R7943, respectively (FIGS. 7g, h, and i).

An Allosteric Site on NKA $\beta_1$ Subunit.

Figure 5:
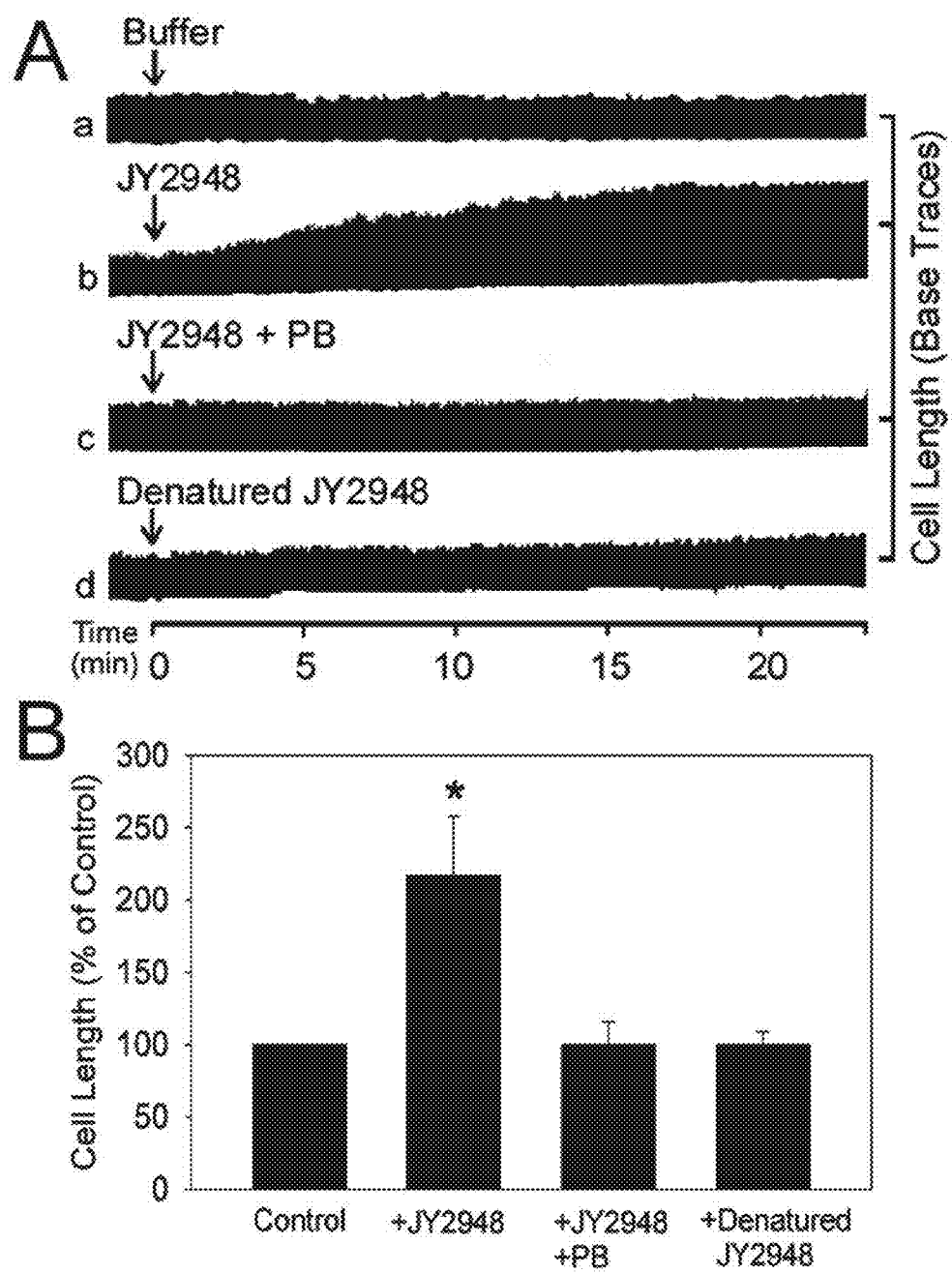
FIG. 5. Allosteric effect of the NKA $\beta_1$ subunit on rat myocyte contractility. (A) Original tracing illustrate the contraction of each rat myocytes: a) Control cell, b) with JY2948, c) a mixture of PB2948 and JY2948, and d) with denatured JY2948. The final concentrations of PB2948 and JY2948 were 0.1 mM and 0.5 μM respectively. (B) Average changes of cell contraction. Myocytes contraction amplitude was expressed by the cell length. Data are presented as % of control based on 6 independent measurements. The results show that binding of JY2948 to NKA β1 subunit increases heart cell contraction.

For the first time, our study identified an allosteric site (FIG. 1A), which resides in the native NKA $\beta_1$ subunit (FIGS. 1B and C) and is capable of remotely controlling the NKA catalytic function (FIG. 2) and enzyme-mediated cardiac cell contraction (FIG. 5). These novel findings critically relied on a natural specific JY2948-$\beta_1$-$\alpha_1$ interaction complex. Confocal immunofluorescence image (FIG. 1B) and Western blots (FIG. 1C) are able to indicate only the location and specific interaction between JY2948 and NKA $\beta_1$ subunit. Alterations of NKA catalytic function, induced by the JY2948-$\beta_1$ interaction, must be through a JY2948-$\beta_1$-$\alpha_1$ intermediate since the a subunit is the sole subunit capable of catalyzing the hydrolysis of ATP and active transport of Na$^+$/K$^+$ ions (23). Considering the $^{134}$KERGEFNHERGER$^{146}$ region (FIG. 1A, rat sequence numbering) i) is not an active site (ATP binding site), nor Na$^+$/K$^+$ ion binding site, ii) is located on extracellular side of the $\beta_1$ subunit (FIG. 1B) and physically distinct from the ATP binding site which exists on the intracellular side of the α subunit, and iii) has striking power to modulate catalytic function of the α subunit, all these facts demonstrate that this antigenic site of JY2948 is an allosteric site of the $\beta_1$ subunit. Furthermore, antibody JY2948 is not a NKA substrate. Specific binding to the $\beta_1$ allosteric site enhances the native activity of NKA, strongly demonstrating that $\beta_1$ subunit possesses allosteric property and that JY2948 is an allosteric activator for both ouabain-resistant and ouabain-sensitive NKA (FIG. 2A-B). Although this particular $\beta_1$ allosteric site is not present in $\beta_2$ and $\beta_3$ isoforms, we do not rule out the possibility that the isoforms of $\beta_1$ subunit might have different allosteric sites for regulating enzyme activity.

Characteristics of $\beta_1$ Subunit Allosteric Property.

The kinetic parameters listed in Table 1 reveal the characteristics of $\beta_1$ allosteric site-induced modulation on NKA function. Experimental results show that V$_{max}$ was 1.69- and 2.47-fold for purified rat and dog NKA enzymes in the presence of JY2948 (FIG. 2C-D). The same holds true for NKA turnover number (K$_{cat}$). Following the specific binding of JY2948 to the $\beta_1$ allosteric sites, K$_{cat}$ was increased 1.69- and 2.44-fold for rat NKA and dog NKA, respectively (FIG. 2C-D). No changes of Km$_{ATP}$ were detected for ouabain-resistant rat NKA and ouabain-sensitive dog NKA (FIG. 2C-D). These data definitively demonstrate that $\beta_1$ subunit can produce a unique positive allosteric regulation on NKA catalytic activity without changing Km$_{ATP}$ (FIG. 2C-D). Moreover, approximately 50% decrease in apparent affinity of Na$^+$ and K$^+$ were detected, as compared with the controls (Table 1), indicating a significant increase of apparent affinity of Na$^+$ and K$^+$ for both rat and dog NKA in the presence of JY2948. Experimental results suggest that the accelerated V$_{max}$ and K$_{cat}$, mediated by $\beta_1$ subunit, are critically linked to and dependent on the alterations of the apparent affinities of Na$^+$ and K$^+$ in the NKA catalytic cycles. These fundamental characteristics not only illustrate the allosteric properties of $\beta_1$ subunit, but also provide important insights into the principles of $\beta_1$-produced positive allosteric modulation.

TABLE 1

Kinetic parameters of NKA in the presence and absence of JY2948. The data were based on the experimental results of FIGS. 2-4. All data listed in Table 1 are mean ± SEM. By comparing kinetic parameters between control and samples with 0.5 μM JY2948, Table 1 illustrates the characteristics of NKA $\beta_1$ subunit allosteric property.

| NKA Kinetic Parameters | Ouabain-Resistant Rat NKA | | Ouabain-Sensitive Dog NKA | |
|---|---|---|---|---|
| | Control (n = 5) | +JY2948 (n = 5) | Control (n = 5) | +JY2948 (n = 6) |
| V$_{max}$ (μmol · mg$^{-1}$ · h$^{-1}$) | 344 ± 99 | 583 ± 22 | 1255 ± 252 | 3098 ± 317 |
| K$_{cat}$ (sec$^{-1}$) | 14.1 ± 4.1 | 23.8 ± 1.1 | 51.3 ± 10 | 125 ± 12 |
| Km$_{ATP}$ (mM) | 0.36 ± 0.15 | 0.36 ± 0.04 | 0.34 ± 0.17 | 0.34 ± 0.1 |
| Na$^+$ Affinity (mM) | 8.8 ± 4.0 | 4.2 ± 0.3 | 8.6 ± 2.1 | 4.1 ± 0.1 |
| K$^+$ Affinity (mM) | 1.3 ± 0.2 | 0.61 ± 0.1 | 1.2 ± 0.1 | 0.65 ± 0.1 |

$\beta_1$ Subunit Allosteric Regulation on Myocyte Contractility.

Unlike digitalis and cardiac glycosides that increase cardiac contraction based on the inhibition of NKA (24), our previous works have demonstrated that activation of NKA (increasing the native activity of the enzyme) induces positive inotropic effect (19). NKA $\beta_1$ subunit produces positive allosteric regulation on enzymatic function (FIGS. 2-4), suggesting that it is likely that the $\beta_1$ subunit may also be able to increase cardiac cell contraction. FIG. 5 shows a 3-fold increase of rat myocyte contraction in the presence of JY2948, demonstrating that $\beta_1$ subunit is indeed capable of regulating cardiac contraction through the activation of NKA.

Fundamental Difference Between $\beta_1$ Subunit- and Ouabain-Mediated $^{45}$Ca Influx.

Figure 6:
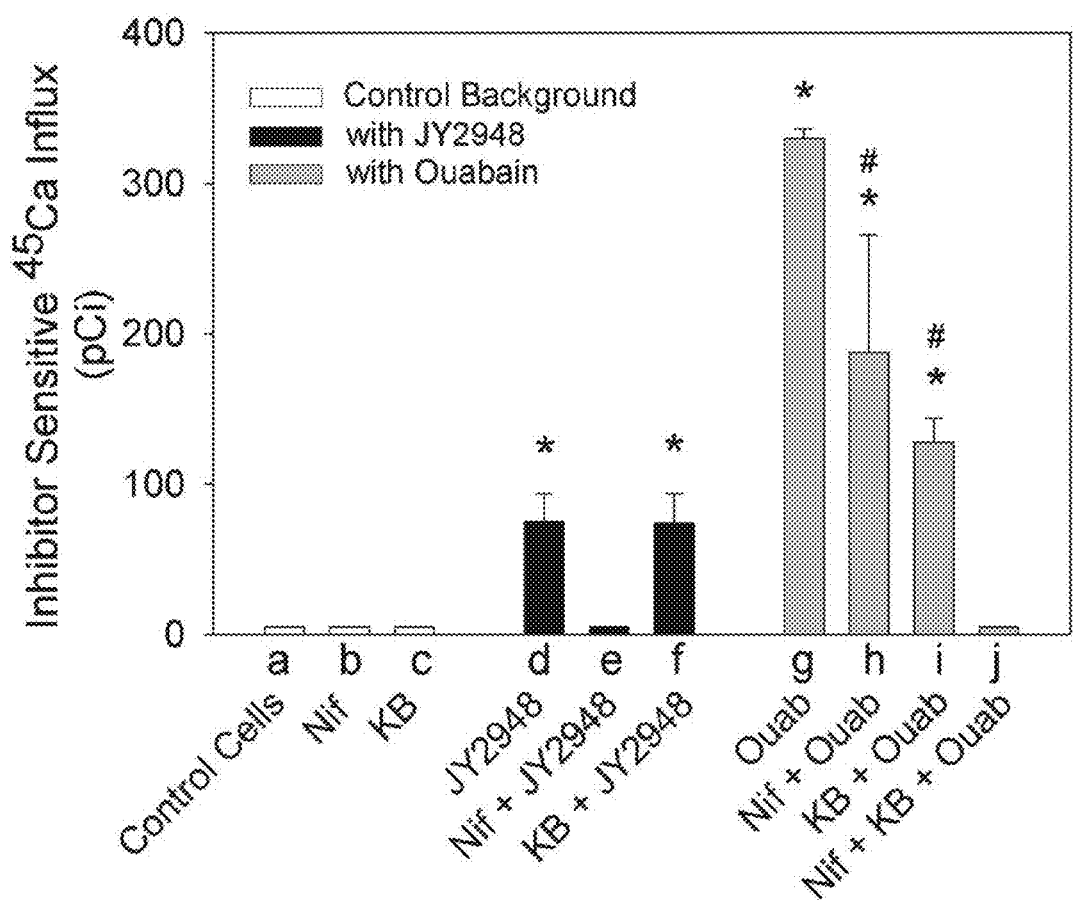
FIG. 6. Allosteric impact of β1 subunit on nifedipine and KB-R7943 sensitive $^{45}$Ca influx. Isolated rat myocytes were incubated with 20 nCi $^{45}$Ca and 10 μM CaCl$_2$ for 60 min at RT in the presence and absence of 1 μM JY2948 or 2.5 mM ouabain with and without 10 μM nifedipine or 5 μM KB-R7943 or both. a) Control myocytes, b) a+nifedipine, c) a+KB-R7943, d) a+JY2948, e) d+nifedipine, f) d+KB- R7943, g) a+ouabain, h) g+nifedipine, i) g+KB-R7943, j) g+nifedipine+KB-R7943. All data represent mean±SEM values of three independent experiments. *P<0.01: Data compared with control background a. #P<0.01: Data compared with g. There is no significant difference between d and f.

Ca$^{2+}$ plays an important role in cardiac contraction. To understand the $\beta_1$ subunit-mediated positive inotropic effect, we performed nifedipine and KB-R7943 sensitive $^{45}$Ca influx experiments on isolated rat myocytes in the presence of JY2948 or ouabain. FIG. 6 shows that the binding of JY2948 to $\beta_1$ subunit caused a 74.9±19 pCi $^{45}$Ca influx into the cell (FIG. 6d). However, nifedipine completely blocked JY2948-induced $^{45}$Ca influx (FIG. 6e), suggesting that LTCC is linked to and responsible for the moderate increase of intracellular Ca$^{2+}$ for $\beta_1$ subunit-mediated positive inotropic effect. NCX inhibitor KB-R7943 failed to inhibit $^{45}$Ca influx (FIG. 6f), suggesting that NCX is not involved in the JY2948-induced $^{45}$Ca influx and implying the absence of reverse-mode of NCX. In contrast, ouabain induced a 330±6.4 pCi $^{45}$Ca influx (FIG. 6g), which is 4.4-fold higher than the one by $\beta_1$ subunit (FIG. 6d). Furthermore, experimental results show that individual nifedipine or KB-R7943 failed to completely inhibit ouabain-induced $^{45}$Ca influx (FIGS. 6h and i), and that approximately 40% of $^{45}$Ca influx was through LTCC (FIG. 6h) and 60% was through NCX (FIG. 6i), suggesting that both LTCC and NCX contribute to the ouabain-induced $^{45}$Ca influx and that NCX may bear a major responsibility in the mechanism of ouabain-induced $Ca^{2+}$ overload. $^{45}$Ca influx was completely abolished in the presence of both nifedipine and KB-R7943 (FIG. 6j), further confirming that ouabain-induced $^{45}$Ca influx was through LTCC and NCX. Taken together, these results demonstrate a fundamental difference between $\beta_1$ subunit- and ouabain-mediated positive inotropy in $Ca^{2+}$ signaling mechanism. It has been reported that cardiac glycosides-induced $Ca^{2+}$ influx via NCX reverse-mode is involved in potentially arrhythmogenic $Ca^{2+}$ overload (25). The fact that NKA β1 subunit modulates a moderate $Ca^{2+}$ influx independent of NCX reverse-mode, can provide a new clinical strategy for the treatment of heart failure to avoid $Ca^{2+}$ overload-mediated arrhythmia.

Important Role of NCX Forward-Mode in $Na^+$ Homeostasis for $\beta_1$ Subunit Allosteric Regulation.

Figure 7:
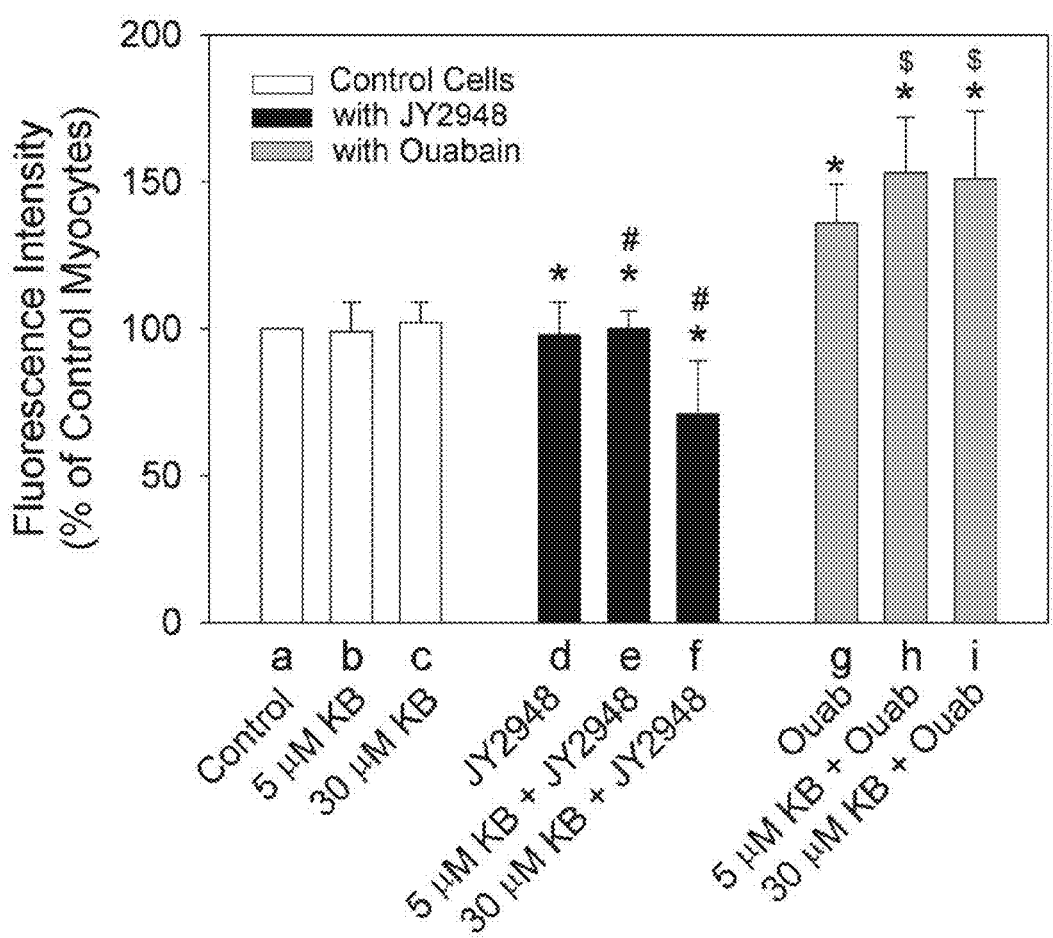
FIG. 7. Allosteric regulation of β1 subunit does not alter intracellular $Na^+$ homeostasis. Isolated rat cardiac myocytes were loaded with cell-permeating Sodium Green dye with or without JY2948 or ouabain in the presence and absence of 5 μM or 30 μM KB-R7943 as indicated in the figure. Fluorescence was measured using a VICTOR-II multilabel counter. Each data point represents the mean±SEM of three independent experiments. *P<0.01: Data compared with control background a. #P<0.01: Data compared with d. $P<0.01: Data compared with g.

Antiporter membrane protein NCX also contributes to $Na^+$ homeostasis by removing a single $Ca^{2+}$ ion out of the cell in exchange for the import of three $Na^+$ ions. However, NCX operates in both forward and reverse directions, depending on the intracellular $Na^+$ and $Ca^{2+}$ gradients (26). It is well known that inhibition of NKA by ouabain causes increase in intracellular $Na^+$ concentration, which initiates the reverse-mode of NCX (24). Would NKA $\beta_1$ subunit-mediated positive inotropic effect increase intracellular $Na^+$ concentration? Which mode of NCX participates in the mechanism of $\beta_1$ subunit-mediated positive inotropy? FIG. 7 provides direct evidence to answer these questions. Binding of JY2948 to NKA $\beta_1$ subunit did not alter $Na^+$ homeostasis (FIG. 7d) compared with control cells (FIG. 7a), demonstrating that $\beta_1$ subunit-mediated positive inotropic effect did not cause increase of intracellular $Na^+$ concentration. No changes of intracellular Na concentration was detected in the presence of 5 μM KB-R7943 (FIG. 7e), suggesting the absence of reverse-mode function of NCX in the $\beta_1$ subunit-mediated positive inotropic effect. However, inhibition of NCX forward-mode by 30 μM of KB-R7943 caused a 29% reduction of fluorescence intensity (FIG. 7f) in the presence of JY2948, suggesting that increasing the rate of NKA ion active transport by $\beta_1$ subunit allosteric regulation may have a tendency to decrease the intracellular $Na^+$ and indicating that NCX may play an important role in maintaining $Na^+$ homeostasis during $\beta_1$ subunit-mediated cellular activities. In contrast, ouabain (2.5 mM) induced a significant increase in intracellular $Na^+$ (FIG. 7g), which is the result of the inactivation of NKA. While no NCX forward-mode is present in the presence of 2.5 mM ouabain, low and high concentrations of KB-R7943 failed to block the increase of $Na^+$ (FIGS. 7h and i), presumably due to a blockade of $Na^+$ extrusion from cardiac myocytes by the reverse-mode function of NCX under the inhibition of NKA conditions. These experimental results suggest that NCX plays fundamental different roles in the mechanisms of Na signaling for NKA β1 subunit- and ouabain-induced positive inotropy.

Antibody JY421228

To further explore the potential allosteric property of NKA $\beta_1$ subunit, monoclonal antibody JY421228 was generated against the $^{218}$RDEDKDKVGNIEY$^{230}$ peptide (SEQ ID NO:3), which resides within the primary sequence of rat NKA $\beta_1$ protein. Amino acid sequence comparison reveals that the antigenic site of JY421228 is highly conserved within the human NKA $\beta_1$ subunit ($^{217}$RDEDKDKVGN-VEY$^{229}$ (SEQ ID NO:4)).

NKA activity is a function of the concentration of JY421228.

Figure 8:
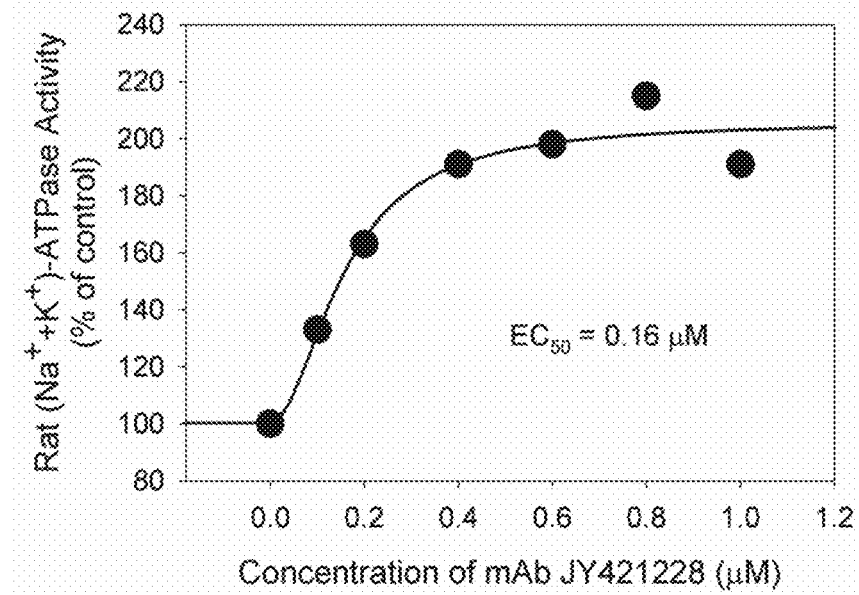
FIGS. 8-9. Monoclonal antibody JY421228 increases NKA ATPase activity. Purified cardiac rat NKA (7.5 μg/ml) and human NKA (2.5 μg/ml) were incubated with different concentrations of antibody JY421228 separately as indicated in the figures for 60 min prior to ouabain-sensitive ATPase assay in the presence of 100 mM $Na^+$, 20 mM $K^+$, and 3 mM ATP. The half maximal effective concentration ($EC_{50}$) of JY421228 was 0.16 μM for rat NKA (FIG. 9) and 0.14 μM for human NKA (FIG. 10).
Figure 9:
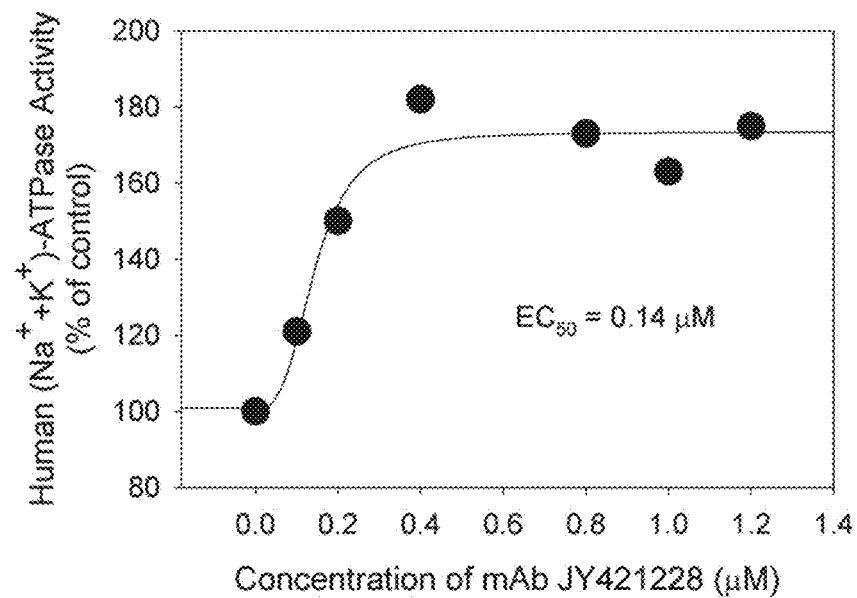

Purified cardiac rat NKA (7.5 μg/ml) and human NKA (2.5 μg/ml) were incubated with different concentrations of JY421228 separately for 60 min prior to ouabain-sensitive ATPase assay in the presence of 100 mM $Na^+$, 20 mM $K^+$, and 3 mM ATP. The half maximal effective concentration ($EC_{50}$) of JY421228 was 0.16 μM for rat NKA (FIG. 8) and 0.14 μM for human NKA (FIG. 9). The figures represent one of the 4-6 independent measurements.

Time Course of the Effect of JY421228 on Myocyte Contractility.

Figure 10:
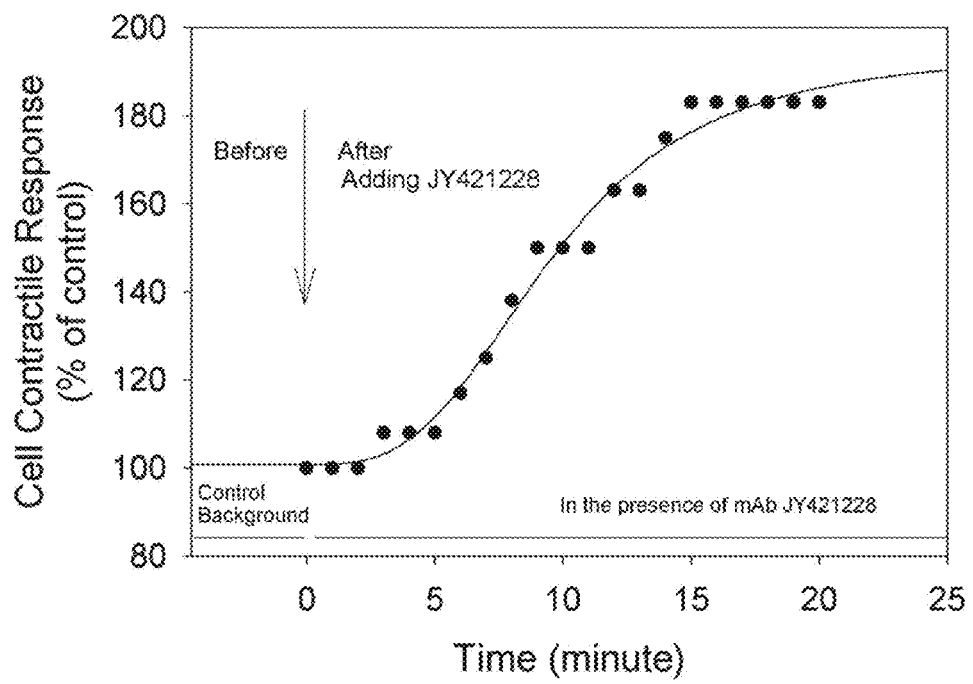
FIG. 10. Time course of the effect of JY421228 on rat myocyte contractility. Increased rat myocyte contraction is a function of time in the presence of 0.5 μM JY421228. Data are presented as % of control cell contractility based on 3 independent measurements.

Increased rat myocyte contraction is a function of time in the presence of 0.5 μM JY421228. Data are presented as % of control cell contractility (FIG. 10). The data shown in FIG. 10 represent one of the five independent measurements.

Figure 11:
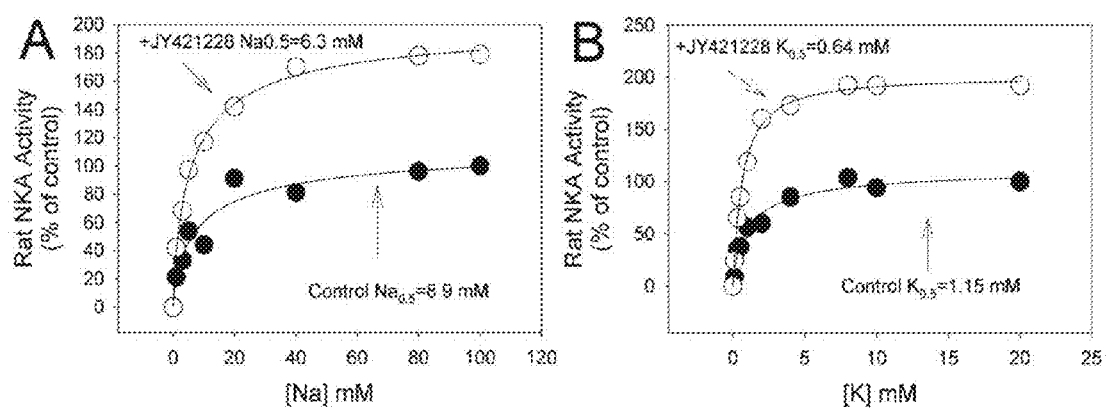
FIG. 11. Effects of JY421228 on NKA $Na^+$ and $K^+$ affinities. A: Purified rat NKA was incubated with JY421228 prior to ouabain-sensitive ATPase assay in the presence of different concentrations of Na and fixed concentrations of $K^+$ (20 mM) and ATP (3 mM). B: Ouabain-sensitive ATPase assay was performed with rat NKA in the presence of different concentrations of $K^+$ and a fixed concentration of $Na^+$ (100 mM). Binding of JY421228 to β₁ subunit increases the NKA $Na^+$ and $K^+$ affinities.

The effects of JY421228 on NKA Na and K affinities are shown in FIG. 11. A: Purified rat NKA was incubated with JY421228 prior to ouabain-sensitive ATPase assay in the presence of different concentrations of Na and fixed concentrations of K (20 mM) and ATP (3 mM). B: Ouabain-sensitive ATPase assay was performed with rat NKA in the presence of different concentrations of K and a fixed concentration of Na (100 mM). The data represent mean of three independent experiments.

Passive Immunization Using an Anti-NKA Alpha Subunit Antibody (SSA412)

Antibodies that specifically bind to the alpha subunit of NKA have been produced and such antibodies have been found to have NKA agonist activity in vivo. Such antibodies are disclosed in U.S. Pat. No. 7,754,210, the entire disclosure of which is incorporated herein by reference in its entirety.

The NKA alpha subunit antibodies were used in experiments conducted to study the effects of passive immunization in mice, that is, to study the effects of administering anti-NKA alpha subunit antibodies to a subject, as described in the following paragraphs. In view of the similarity of in vitro activity between anti-NKA alpha subunit antibodies and anti-NKA $\beta_1$ subunit antibodies, the anti-NKA beta subunit antibodies are expected to induce in vivo effects similar to those induced by the anti-NKA alpha subunit antibodies.

Measurement of Mouse Myocardial Performance and Cardiovascular Function.

Male wild-type mice (CD1, Charles River, 30-40 g) were utilized for this study. Mouse in vivo cardiac function was assessed by pressure-volume catheter in anesthetized mouse as previously described (26). Mice were anesthetized with a combination of urethane (300-500 mg/kg), etomidate (5 mg/kg) and morphine (0.5 mg/kg) and intubated with a blunt 19 G needle inserted via tracheostomy. Ventilation was initiated with 100% oxygen using a custom-designed, constant flow ventilator delivering a tidal volume of 6.7 μl/kg at 120 breaths per min. The left external jugular vein was cannulated with a 30 G needle connected to an infusion pump. Modest volume expansion was provided (150 μl of 12.5% human albumin) at 50 μl/min. Following stabilization, a lateral incision was made at the xyphoid cartilage to expose the left ventricular (LV) apex. The 1.4 F pressure-volume catheter (SPR-839, Millar Instruments Inc., Houston, Tex., USA) was inserted via an apical puncture with a 26 G needle, and advanced along the cardiac long axis. A 2 F pacing catheter (NuMed, Nicholville, N.Y., USA) was placed in the esophagus, dorsal to the left atrium. To avoid the force-frequency effects during the measurements of cardiac contraction and relaxation, the atrium was paced at 600 beats per minute (bpm) with 5-7 V, 2 ms pulses (SD25, Grass Instruments, Quincy, Mass., USA). Calibration of the volume signal was performed using a 5-10 µl bolus of 30% hypertonic saline injected into the jugular vein to determine the signal offset and an ultrasound flow probe (AT01RB, Transonic Systems Inc.) placed around the thoracic aorta to determine signal gain. Data were digitized at 2 kHz and stored to disk for off-line analysis.

PBS was infused for 10 min prior to infusion of anti-NKA alpha subunit antibody (SSA412) for 30 min, followed by a 30-40 min washout (depending on the weight of the animal) with PBS. The final concentration of SSA412 antibody was approximately 0.32 µM (µmoles of SSA412/ml of mouse total blood volume). The rate of both infusion and washout was at 5 µl/min. Indexes of myocardial systolic and diastolic parameters were obtained every minute at steady state and during occlusion of the inferior vena cava every 5 minutes. Steady-state was derived from 10 consecutive averaged beats. Cardiac preload was indexed as the left ventricular end-diastolic volume (EDV). Cardiac afterload was evaluated as end-systolic pressure (ESP). Load independent systolic function was assessed by end-systolic elastance (Ees), preload-recruitable stroke work (PRSW), maximal rate of pressure rise normalized to instantaneously developed pressure ($dP/dt_{max}/IP$) while ventricular relaxation was estimated using the time constant of pressure relaxation (Tau) and $dP/dt_{min}$.

Activation of NKA Induces Positive Inotropic Effect on Mouse Heart In Vivo.

Figure 12:
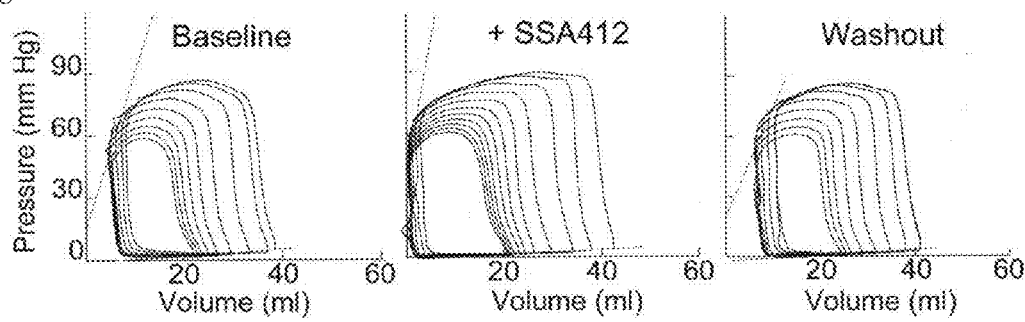
FIG. 12. Representative pressure-volume loops during preload reduction by IVC occlusion showing the effect of NKA alpha-subunit antibody SSA412 on intact mouse heart. SSA412 was administered intravenously at a rate of 5 μl/min. A) Control background. B) Presence of SSA412 (peak response). C) Following wash with PBS. The results show that SSA412 induces positive inotropic effect as demonstrated by the leftward shift of the PV loop with increased end-systolic elastance (Ees, slope of upper left curve).

To examine the effect of activation of NKA on intact mouse heart, we used a micromanometer-conductance catheter and assessed the hemodynamic parameters obtained from pressure-volume (PV) loop analysis. Following administration of SSA412, PV loop shifted leftward with enhanced end-systolic elastance (FIG. 12, middle panel, shown as left upper relations) and increased stroke volume (loop width) as compared with the control background (FIG. 12A), which represent positive inotropy occurring in mouse heart in vivo (FIG. 12B). This in vivo positive inotropic effect started about 10-15 minutes after administration of SSA412 and reached its maximum after 20 minutes. Activation of NKA-induced positive inotropy gradually disappeared following PBS wash (FIG. 12C), indicating a reversible positive inotropic effect in intact animal heart.

Figure 13:
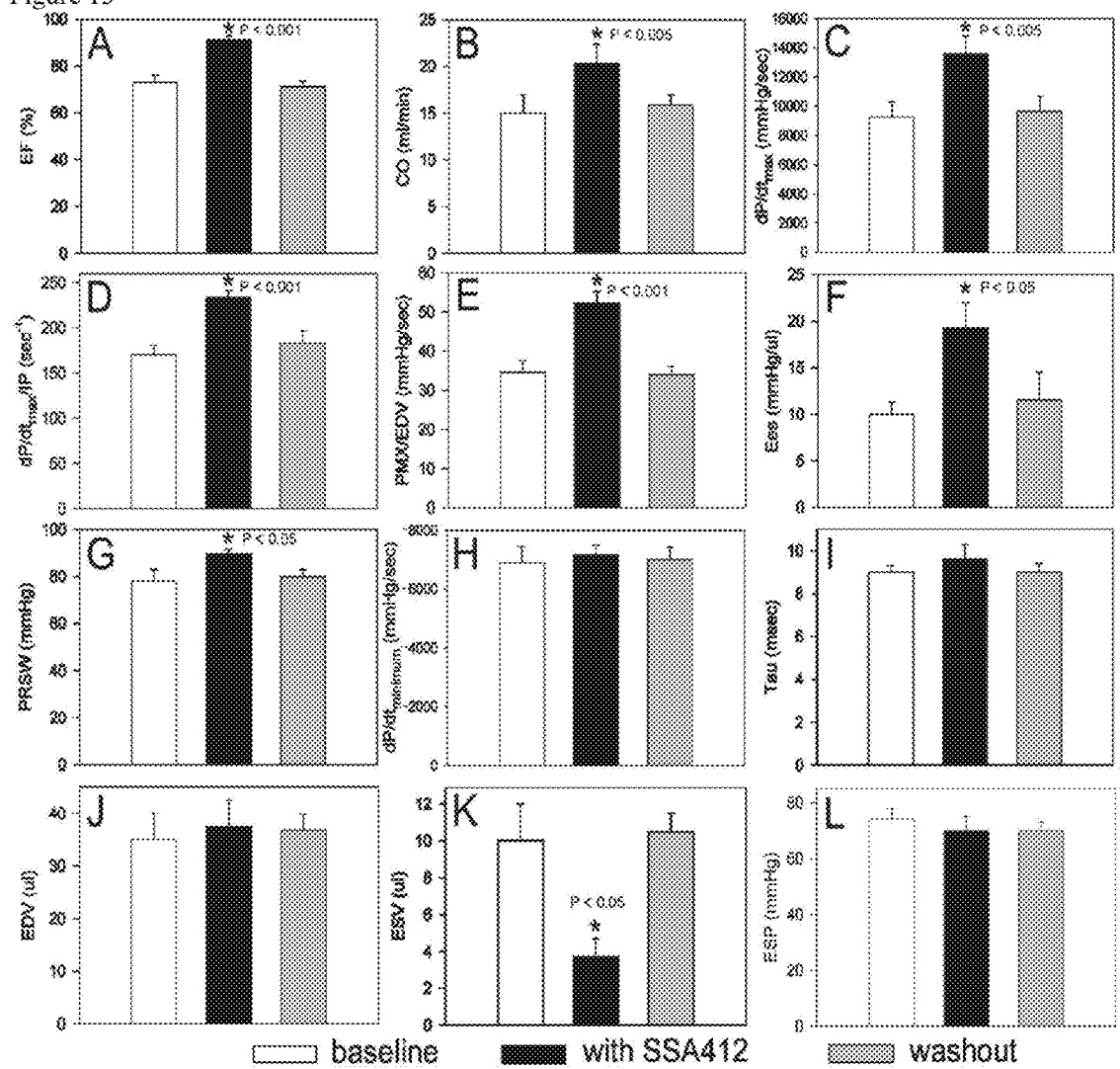
FIG. 13. Analysis of hemodynamic effects of SSA412 on mouse heart (n=5). Data are mean±sem. EDV-LV: end-diastolic volume; ESV-LV: end-systolic volume; ESP: end-systolic pressure; EF: ejection fraction; CO: cardiac output; $dP/dt_{max}$: maximal rate of pressure rise; $dP/dt_{max}/IP$-$dP/dt_{max}$: normalized to instantaneous developed pressure; PMX/EDV: maximal ventricular power divided by EDV; Ees: end-systolic elastance; PRSW: preload recruitable stroke work; Tau: time constant of pressure relaxation derived using monoexponential fit; $dP/dt_{minimum}$: peak rate of LV pressure decline. Significance of the P-values is indicated in the Figure. SSA412 increased the strength of cardiac contraction, thereby decreasing the end-systolic volume (ESV; see panel K, bottom panel of middle column).

Detailed cardiac parameters were obtained from PV loop analyses as shown in FIG. 13. Following administration of SSA412, global systolic functions such as ejection fraction (EF) and cardiac output (CO) increased 25% and 38%, respectively, as compared with the control. These increments vanished after washout (FIGS. 13A & B). Isovolumic cardiac contractile parameters $dP/dt_{max}$, $dP/dt_{max}/IP$ ($dP/dt_{max}$ normalized by instantaneous pressure), and PMX/EDV ($dP/dt_{max}$ normalized by power index) all augmented 41%, 40%, and 51%, respectively, in the presence of SSA412 (FIGS. 13C, D & E). Load-independent indices of cardiac contractility such as Ees and preload recruitable stroke work (PRSW) were also elevated by SSA412 administered (FIGS. 13F & G). In contrast, relaxation indexes such as $dP/dt_{minimum}$, or Tau were not altered by the antibody (FIGS. 13H & I). End-systolic volume (ESV) decreased (FIG. 13K), but no change in end-diastolic volume (EDV) was noticed (FIG. 13J), suggesting that SSA412 had no effect on cardiac preload. No significant change in end-systolic pressure (ESP) was observed (FIG. 13L).

These in vivo animal studies revealed that activated NKA, induced by antibody SSA412, markedly generates a reversible positive inotropic effect in mouse heart (FIGS. 12 & 13), while control buffer PBS at the infusion rate did not alter myocardial performance and cardiovascular function, indicating the specificity of the biological action of activation of NKA in vivo. Moreover, global systolic parameters, such as EF and CO, and specific contractile parameters including dP/dtmax, dP/dtmax/IP, PMX/EDV, Ees, and PRSW, all substantially increased following administration of SSA412 (FIG. 13), demonstrating a dramatic change in mouse heart presumably caused by interaction between SSA412 and the D-R region of the H7-H8 domain of NKA. Significant increase in specific load independent parameters such as $dP/dt_{max}/IP$ and PMX/EDV without changing cardiac load confirms that positive inotropy induced by SSA412 is purely cardiac effect (FIGS. 13D, E, J and L). These in vivo results provide the first physiological evidence that activation of NKA is capable of inducing a primary positive inotropy in intact mouse heart in vivo. The experimental results provide the evidence demonstrating that activation of NKA induces a significant positive inotropic effect in intact mouse heart in vivo.

Activation of NKA Regulates Cardiac Function in Intact Mouse Heart.

In vivo animal studies reveal that activated NKA, induced by an anti-NKA $\beta_1$ subunit antibody, markedly generates a reversible positive inotropic effect in mouse heart, while control buffer PBS at the infusion rate does not alter myocardial performance and cardiovascular function, indicating the specificity of the biological action of activation of NKA in vivo. Moreover, global systolic parameters, such as EF and CO, and specific contractile parameters including dP/dtmax, dP/dtmax/IP, PMX/EDV, Ees, and PRSW, all substantially increase following administration of an anti-NKA $\beta_1$ subunit antibody, demonstrating a dramatic change in mouse heart presumably caused by interaction between the antibody and the NKA $\beta_1$ subunit. Significant increase in specific load independent parameters such as $dP/dt_{max}/IP$ and PMX/EDV without changing cardiac load confirms that positive inotropy induced by anti-NKA $\beta_1$ subunit antibodies is a purely cardiac effect.

Figure 14:
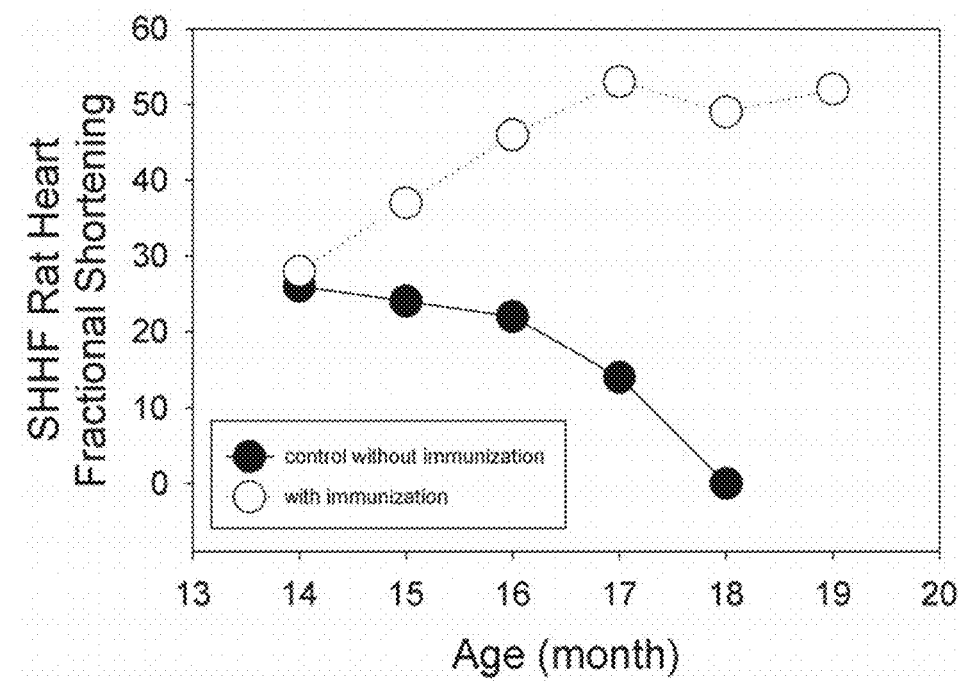
FIG. 14. Therapeutic effect of endogenous inotropic antibody on the late-stage Spontaneously Hypertensive Heart Failure (SHHF) rats is shown. The results show that generation of endogenous NKA antibody significantly improved the condition of the late-stage SHHF rat cardiac function (open circles) while the control rat without immunization (black circles) died.

Studies were also conducted on the ability of NKA alpha subunit peptides to induce a therapeutic immune response in late-stage Spontaneously Hypertensive Heart Failure (SHHF) rats. The SHHF rats used for this study were 14 months old with late-stage heart failure. The heart function was measured by echo and expressed as percent of fractional shortening (FS %). The initial heart functions were 26.0% and 28.0% for control SHHF rat and the one with immunization, respectively. The results (FIG. 14) show that generation of endogenous NKA antibody significantly improved the condition of the late-stage SHHF rat cardiac function (open circles) while the control rat without immunization (black circles) died. The peptide with which the rats were immunized has the following amino acid sequence DVEDSYGQQWTYEQR (SEQ ID NO:7), as disclosed in U.S. Pat. No. 7,754,210.

In view of the similarity of in vitro activity between anti-NKA alpha subunit antibodies and anti-NKA $\beta_1$ subunit antibodies, the anti-NKA $\beta_1$ subunit peptides are expected to induce in vivo effects similar to those induced by the anti-NKA alpha subunit peptides.

REFERENCES

All patents and publications mentioned in this specification are indicative of the level of skill of those skilled in the art to which the invention pertains. Each cited patent and publication is incorporated herein by reference in its entirety. All of the following references have been cited in this application:
1. Skou J C (1998) Nobel Lecture. The identification of the sodium pump. Biosci Rep 18(4):155-169.
2. Kyte J (1981) Molecular considerations relevant to the mechanism of active transport. Nature 292(5820):201-204.
3. Allen D G, Eisner D A, & Wray S C (1985) Birthday present for digitalis. Nature 316(6030):674-675.
4. Smith T W (1988) Digitalis. Mechanisms of action and clinical use. N Engl J Med 318(6):358-365.
5. Marban E S T (1992) Digitalis (Raven Press, New York).
6. Blanco G, DeTomaso A W, Koster J, Xie Z J, & Mercer R W (1994) The alpha-subunit of the Na,K-ATPase has catalytic activity independent of the beta-subunit. J Biol Chem 269(38):23420-23425.
7. Xu K Y (2005) Activation of (Na++K+)-ATPase. Biochem Biophys Res Commun 338(4):1669-1677.
8. Schneider J W, et al. (1985) Molecular cloning of rat brain Na,K-ATPase alpha-subunit cDNA. Proc Natl Acad Sci USA 82(18):6357-6361.
9. Shull G E, Greeb J, & Lingrel J B (1986) Molecular cloning of three distinct forms of the Na+,K+-ATPase alpha-subunit from rat brain. Biochemistry 25(25):8125-8132.
10. Sverdlov E D, et al. (1987) The family of human Na+,K+-ATPase genes. No less than five genes and/or pseudogenes related to the alpha-subunit. FEBS Lett 217(2):275-278.
11. Blanco G, Sanchez G, Melton R J, Tourtellotte W G, & Mercer R W (2000) The alpha4 isoform of the Na,K-ATPase is expressed in the germ cells of the testes. J Histochem Cytochem 48(8):1023-1032.
12. Martin-Vasallo P, Dackowski W, Emanuel J R, & Levenson R (1989) Identification of a putative isoform of the Na,K-ATPase beta subunit. Primary structure and tissue-specific expression. J Biol Chem 264(8):4613-4618.
13. Gloor S, et al. (1990) The adhesion molecule on glia (AMOG) is a homologue of the beta subunit of the Na,K-ATPase. J Cell Biol 110(1):165-174.
14. Malik N, Canfield V A, Beckers M C, Gros P, & Levenson R (1996) Identification of the mammalian Na,K-ATPase 3 subunit. J Biol Chem 271(37):22754-22758.
15. Besirli C G, Gong T W, & Lomax M I (1997) Novel beta 3 isoform of the Na,K-ATPase beta subunit from mouse retina. Biochim Biophys Acta 1350(1):21-26.
16. Hoffman, B F & J T Bigger Jr (1980) "Digitalis and Allied Cardiac Glycosides" in The Pharmacological Basis of Therapeutics, eds. Goodman and Gilman, p. 732.
17. Kyte J (1971) Purification of the sodium- and potassium-dependent adenosine triphosphatase from canine renal medulla. J Biol Chem 246(13):4157-4165.
18. Wang S Q, Song L S, Lakatta E G, & Cheng H (2001) Ca2+ signalling between single L-type Ca2+ channels and ryanodine receptors in heart cells. Nature 410(6828):592-596.
19. Xu K Y (2005) Activation of (Na++K+)-ATPase. Biochem Biophys Res Commun 338(4):1669-1677.
20. Xu K Y, Zhu W, & Xiao R P (Serine496 of beta2 subunit of L-type Ca2+ channel participates in molecular crosstalk between activation of (Na++K+)-ATPase and the channel. Biochem Biophys Res Commun 402(2):319-323.
21. Xu K Y, Takimoto E, & Fedarko N S (2006) Activation of (Na++K+)-ATPase induces positive inotropy in intact mouse heart in vivo. Biochem Biophys Res Commun 349(2):582-587.
22. Iwamoto T, Watano T, & Shigekawa M (1996) A novel isothiourea derivative selectively inhibits the reverse mode of Na+/Ca2+ exchange in cells expressing NCX1. J Biol Chem 271(37):22391-22397.
23. Blanco G, DeTomaso A W, Koster J, Xie Z J, & Mercer R W (1994) The alpha-subunit of the Na,K-ATPase has catalytic activity independent of the beta-subunit. J Biol Chem 269(38):23420-23425.
24. Marban E S T (1992) Digitalis (Raven Press, New York).
25. Satoh H, et al. (2000) KB-R7943 block of Ca(2+) influx via Na(+)/Ca(2+) exchange does not alter twitches or glycoside inotropy but prevents Ca(2+) overload in rat ventricular myocytes. Circulation 101(12):1441-1446.
25. Pogwizd S M & Bers D M (2002) Na/Ca exchange in heart failure: contractile dysfunction and arrhythmogenesis. Ann N Y Acad Sci 976:454-465.
26. Xu, Y Y (2006) Activation of (Na++K+)-ATPase induces positive inotropy in intact mouse heart in vivo. Biochem Biophys Res Comm 349:582-587.

What is claimed is:

1. A method of producing a positive inotropic effect in a mammalian host comprises administering a pharmaceutically acceptable carrier and a therapeutically effective amount of an antibody or an antigen-binding fragment thereof that specifically binds to one or more epitopes of the β1 subunit of the $(Na^{+}+K^{+})$-ATPase to said mammalian host, said one or more epitopes are represented by SEQ ID NOS: 1-6.

2. The antibody of claim 1, wherein the antibody is a polyclonal antibody, a monoclonal antibody, or a humanized antibody.

3. The method of claim 1, wherein said antibody is IgG1, IgG2, IgG3, IgG4, IgM, IgA1, IgA2, IgD, IgE, or a single chain antibody.

4. The method of claim 1, wherein said antigen-binding fragment is an Fab fragment or an F(ab')2 fragment.

5. The method of claim 1, wherein the antibody or an antigen-binding fragment thereof is administered in a daily dose of about 10 μg/kg body weight to about 200 μg/kg body weight.

6. The method of claim 1, further comprising monitoring the mammal's cardiac contractions for a positive inotropic effect.

* * * * *

SEQUENCE LISTING

```
<160> NUMBER OF SEQ ID NOS: 7

<210> SEQ ID NO 1
<211> LENGTH: 13
<212> TYPE: PRT
<213> ORGANISM: Rattus norvegicus

<400> SEQUENCE: 1

Lys Glu Arg Gly Glu Phe Asn His Glu Arg Gly Glu Arg
1               5                   10

<210> SEQ ID NO 2
<211> LENGTH: 13
<212> TYPE: PRT
```

```
<213> ORGANISM: Homo sapiens

<400> SEQUENCE: 2

Lys Glu Arg Gly Asp Phe Asn His Glu Arg Gly Glu Arg
1               5                   10

<210> SEQ ID NO 3
<211> LENGTH: 13
<212> TYPE: PRT
<213> ORGANISM: Rattus norvegicus

<400> SEQUENCE: 3

Arg Asp Glu Asp Lys Asp Lys Val Gly Asn Ile Glu Tyr
1               5                   10

<210> SEQ ID NO 4
<211> LENGTH: 13
<212> TYPE: PRT
<213> ORGANISM: Homo sapiens

<400> SEQUENCE: 4

Arg Asp Glu Asp Lys Asp Lys Val Gly Asn Val Glu Tyr
1               5                   10

<210> SEQ ID NO 5
<211> LENGTH: 13
<212> TYPE: PRT
<213> ORGANISM: Canis lupus

<400> SEQUENCE: 5

Lys Glu Arg Gly Glu Phe Asn Asn Glu Arg Gly Glu Arg
1               5                   10

<210> SEQ ID NO 6
<211> LENGTH: 13
<212> TYPE: PRT
<213> ORGANISM: Sus scrofa

<400> SEQUENCE: 6

Lys Glu Arg Gly Glu Tyr Asn Asn Glu Arg Gly Glu Arg
1               5                   10

<210> SEQ ID NO 7
<211> LENGTH: 15
<212> TYPE: PRT
<213> ORGANISM: Artificial Sequence
<220> FEATURE:
<223> OTHER INFORMATION: chemically-synthesized antigen

<400> SEQUENCE: 7

Asp Val Glu Asp Ser Tyr Gly Gln Gln Trp Thr Tyr Glu Gln Arg
1               5                   10                  15
```